United States Patent
Goldfain et al.

(10) Patent No.: US 11,804,124 B2
(45) Date of Patent: *Oct. 31, 2023

(54) REDUCING ILLNESSES AND INFECTIONS CAUSED BY INEFFECTIVE CLEANING BY TRACKING AND CONTROLLING CLEANING EFFICACY

(71) Applicant: Ecolab USA Inc., Saint Paul, MN (US)

(72) Inventors: Albert Goldfain, Chanhassen, MN (US); Gregory Bryant Hayes, Apple Valley, MN (US); Emily Gaynor, Oak Ridge, NC (US); Pedro Van Hoecke, Woodbury, MN (US); Ilona Furman Weart, Farmington, MN (US); Joseph Wegner, Falcon Heights, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/897,330

(22) Filed: Aug. 29, 2022

(65) Prior Publication Data
US 2022/0415157 A1    Dec. 29, 2022

Related U.S. Application Data

(63) Continuation of application No. 16/783,908, filed on Feb. 6, 2020, now Pat. No. 11,430,321.
(Continued)

(51) Int. Cl.
*G08B 21/24*    (2006.01)
(52) U.S. Cl.
CPC ................... *G08B 21/245* (2013.01)
(58) Field of Classification Search
CPC ................. G08B 21/245; G16H 40/20
See application file for complete search history.

(56) References Cited

U.S. PATENT DOCUMENTS 5,966,753 A * 10/1999 Gauthier .................. A47K 5/12
4/628
8,021,312 B2    9/2011 Kinnunen et al.
(Continued)

FOREIGN PATENT DOCUMENTS

CN    204631547 U    9/2015
CN    105528519 A    4/2016
(Continued)

OTHER PUBLICATIONS

Hwang et al., "Wristband-type wearable health devices to measure construction workers' physical demands," Automation in Construction, vol. 83, Nov. 2017, pp. 330-340, Abstract only.
(Continued)

*Primary Examiner* — Sisay Yacob
(74) *Attorney, Agent, or Firm* — Fredrikson & Byron, P.A.

(57) ABSTRACT

A wearable computing device may be used to track the efficacy of one or more cleaning actions performed. The device can include one or more sensors that detect and measure motion associated with a cleaning event. In different examples, the movement data generated by the device can be compared to reference movement data to determine if the individual has cleaned all the objects they were expected to clean and/or if the individual has cleaned a given object sufficiently well. As another example, the movement data generated by the device can be analyzed to distinguish cleaning and non-cleaning movement actions as well as to distinguish different types of cleaning actions during cleaning movement. The quality of each cleaning action can be evaluated. In any configuration, the device may perform an operation in response to determining that ineffective cleaning is being performed, causing corrected cleaning action to be performed.

26 Claims, 18 Drawing Sheets

Related U.S. Application Data

(60) Provisional application No. 62/801,875, filed on Feb. 6, 2019, provisional application No. 62/801,865, filed on Feb. 6, 2019.

(56) References Cited

U.S. PATENT DOCUMENTS

| | | | |
|---|---|---|---|
| 8,294,584 | B2 | 10/2012 | Plost |
| 9,135,805 | B2 | 9/2015 | Freedman et al. |
| 9,466,188 | B2 | 10/2016 | Hamam et al. |
| 9,483,930 | B1 | 11/2016 | Haaland |
| 9,542,828 | B1 | 1/2017 | Haaland |
| 9,727,182 | B2 | 8/2017 | Deokar et al. |
| 9,864,955 | B2 | 1/2018 | Faaborg et al. |
| 9,922,533 | B2 | 3/2018 | Hayes et al. |
| 9,961,189 | B2 | 5/2018 | Kadous |
| 9,977,509 | B2 | 5/2018 | Park et al. |
| 10,004,823 | B2 | 6/2018 | Reid et al. |
| 2009/0195385 | A1 | 8/2009 | Huang et al. |
| 2012/0116803 | A1* | 5/2012 | Reid ............... G16H 40/20 705/2 |
| 2014/0266732 | A1 | 9/2014 | Barbeau et al. |
| 2015/0261519 | A1 | 9/2015 | Hsieh et al. |
| 2016/0125348 | A1 | 5/2016 | Dyer et al. |
| 2016/0148485 | A1* | 5/2016 | Hayes ............... A61L 2/26 340/665 |
| 2016/0275779 | A1 | 9/2016 | Hajdenberg |
| 2016/0328948 | A1 | 11/2016 | Ferniany |
| 2017/0046943 | A1 | 2/2017 | Haaland |
| 2017/0076042 | A1 | 3/2017 | Katz et al. |
| 2017/0124850 | A1 | 5/2017 | Kramer |
| 2017/0227530 | A1* | 8/2017 | Finison ............ G01N 33/6803 |
| 2018/0028038 | A1 | 2/2018 | Setchell et al. |
| 2018/0120794 | A1 | 5/2018 | Cheng et al. |
| 2018/0125623 | A1 | 5/2018 | Serval et al. |
| 2018/0357886 | A1* | 12/2018 | Tavori ............... G16H 40/20 |
| 2019/0008270 | A1 | 1/2019 | Hardeman et al. |

FOREIGN PATENT DOCUMENTS

| | | |
|---|---|---|
| CN | 107224249 A | 10/2017 |
| EP | 3038064 A1 | 6/2016 |
| EP | 2404193 B1 | 5/2017 |
| WO | 2016189358 A1 | 12/2016 |
| WO | 2016209670 A1 | 12/2016 |
| WO | 2017073955 A1 | 5/2017 |
| WO | 2017094016 A1 | 6/2017 |

OTHER PUBLICATIONS

Liu et al., "Significant Change Spotting for Periodic Human Motion Segmentation of Cleaning Tasks Using Wearable Sensors," Sensors (Basel), vol. 17, No. 1, Jan. 2017, 19 pages.

Peixoto et al., "Designing the Smart Badge: A Wearable Device for Hospital Workers," PervasiveHealth '18, 2018, 4 pages.

Pereira et al., "Physical Activity Intensity Monitoring of Hospital Workers using a Wearable Sensor," PervasiveHealth '18, 2018, 4 pages.

International Patent Application No. PCT/US2020/017040, International Search Report and Written Opinion dated May 26, 2020, 18 pages.

International Patent Application No. PCT/US2020/017043, International Search Report and Written Opinion dated May 26, 2020, 18 pages.

* cited by examiner

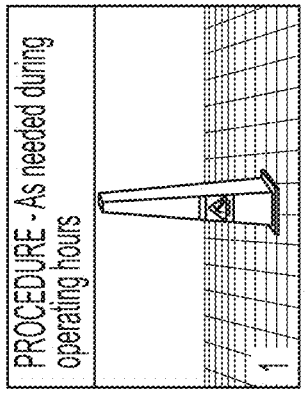
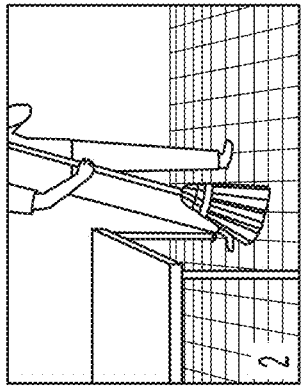
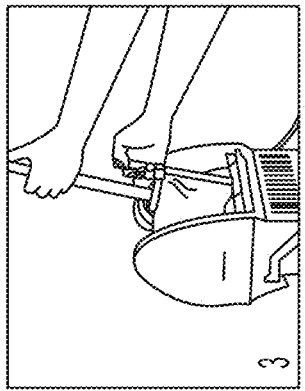
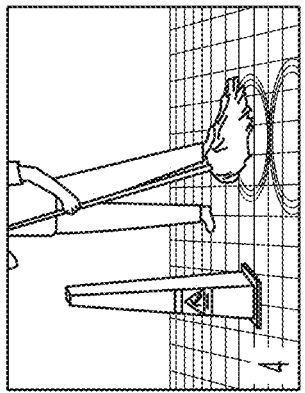
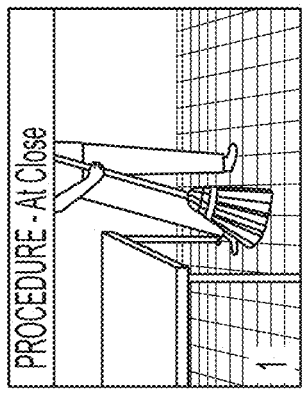
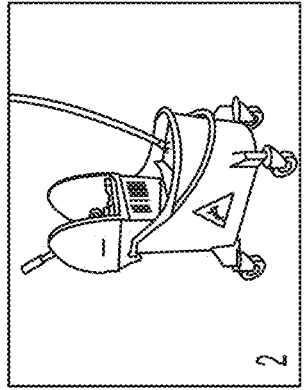
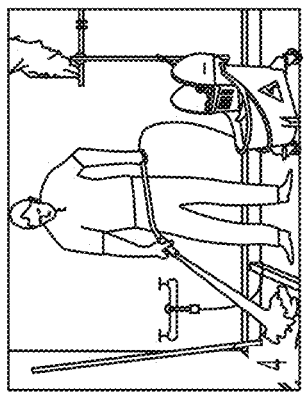
FIG. 3A

BEFORE CLEANING
- Cover and remove any exposed products/raw ingredients from the grill area.
- Turn grill off and disconnect electricity.
- Scrape grill plate.
- Wait 5-10 minutes to cool below 175°C.

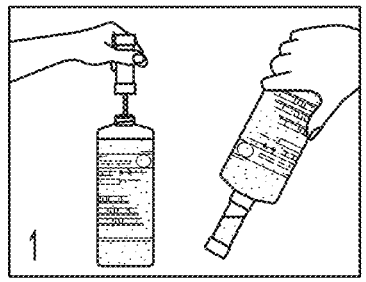

- Dispense 1/2 oz of KAY® QSR Heat-Activated Grill & Toaster Cleaner into measuring cap.

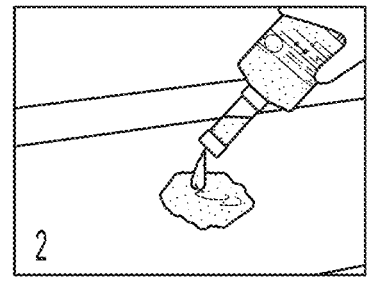

- Wearing heat-resistant gloves, dispense half of the measured product onto the grill cleaning tool and apply to top platen.

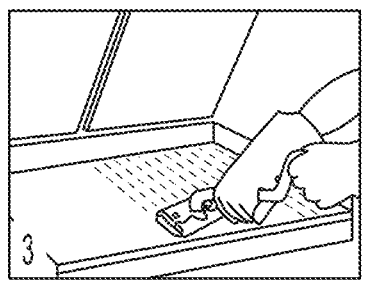

- Repeat previous procedure for bottom platen. Wait 1-2 minutes for product to work on surfaces.

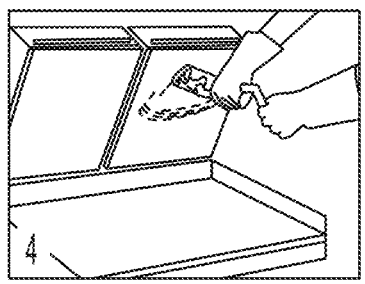

- Scrub surface with cleaning tool in circular motion.

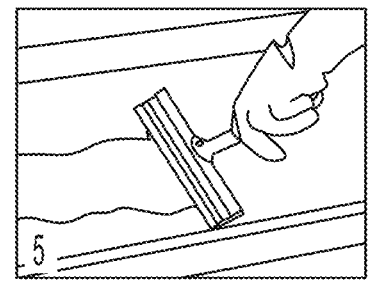

- Pour small amounts of lukewarm water onto surface and scrape into trough; continue to do so until grill cools and remains wet.

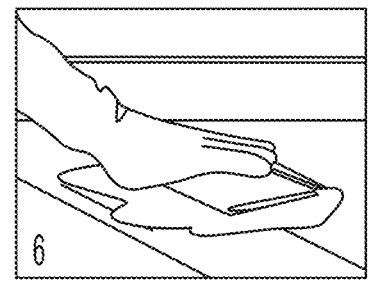

- Still wearing heat-resistant gloves, wipe grill and backsplash with a clean, damp cloth.

FIG. 3B

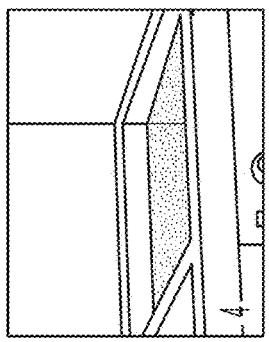
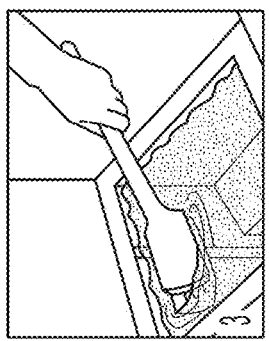
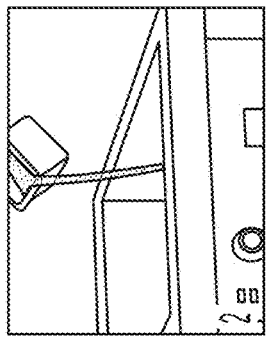
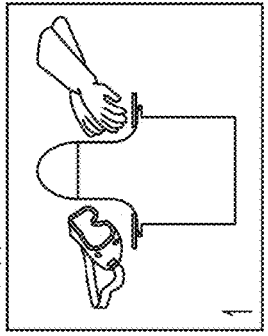
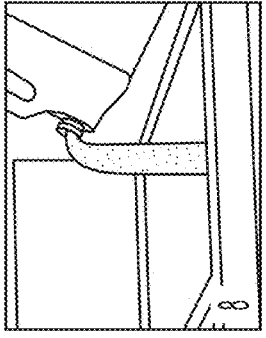
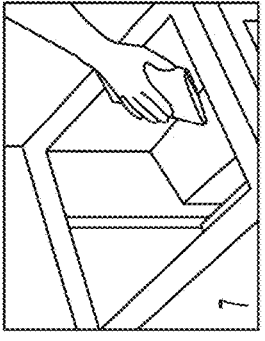
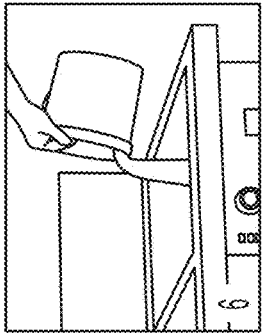
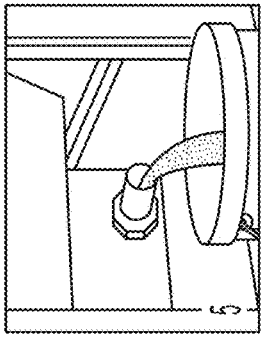
FIG. 3C

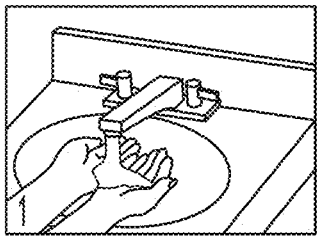

Use water as hot as the hands can comfortably stand (at least 100°F/38°C). Moisten hands.
*Use agua tan caliente como sus manos puedan soportar cómodamente (al menos 100°F/38°C). Humedézcase las manos.*

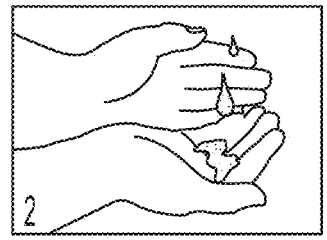

With one push, dispense soap into palm; soap and lather thoroughly to the elbow.
*Ponga jabón en la palma de la mano una sola vez, enjabónese y póngase espuma hasta el codo.*

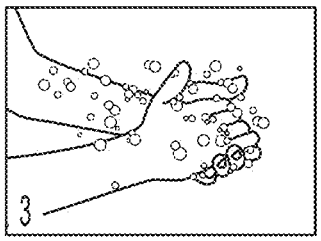

Rub hands together vigorously for 20 seconds. Clean under fingernails and between fingers.
*Frótese las manos enérgicamente durante 20 segundos. Limpiese debajo de las uñas y entre los dedos.*

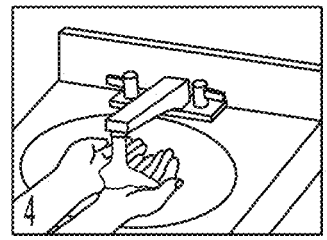

Rinse thoroughly under running water.
*Enjuáguese completamente usando agua corriente.*

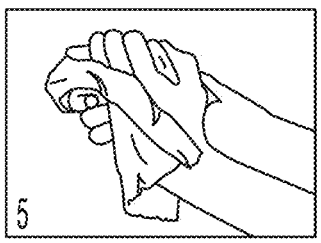

Dry hands using single service towels or hot air dryer. Use your paper towel to turn off water.
*Séquese las manos usando toallas descartables o con una secadora. Utilice su toalla de papel para dar vuelta apagado riegan.*

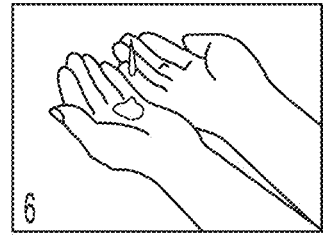

With one push, dispense hand sanitizer into palm; rub hands together covering all surfaces of hands and fingers with sanitizer. Rub until dry (15-20 seconds).
*Ponga sanitizante en la palma de la mano una sola vez, frote las manos juntas cubriendo toda la superficie de las manos y los dedos con sanitizante. Frote hasta que la gel se seque (15-20 segundos).*

FIG. 7

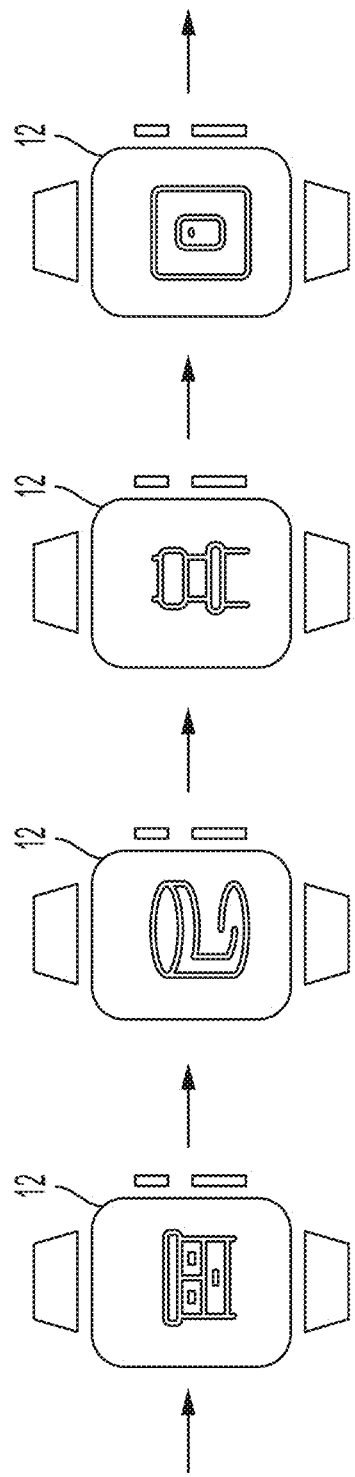

REDUCING ILLNESSES AND INFECTIONS CAUSED BY INEFFECTIVE CLEANING BY TRACKING AND CONTROLLING CLEANING EFFICACY

CROSS-REFERENCE

This application is a continuation of U.S. patent application Ser. No. 16/783,908, filed Feb. 6, 2020, which claims the benefit of U.S. Provisional Patent Application No. 62/801,865, filed Feb. 6, 2019, and U.S. Provisional Patent Application No. 62/801,875, filed Feb. 6, 2019. The entire contents of each of these applications are incorporated herein by reference.

TECHNICAL FIELD

This disclosure relates to devices and techniques for reducing illnesses and infections caused by ineffective cleaning, including monitoring and controlling of cleaning efficacy through a wearable computing device worn by an individual performing cleaning.

BACKGROUND

Ineffective cleaning is one of the leading causes of pathogen transmission, resulting in illnesses and infections for millions annually. For example, the United States Centers for Disease Control and Prevention estimates that 48 million people annually get sick in the United States due to food-borne illness, leading to 128,000 hospitalizations and 3000 deaths. Further, the World Health Organization estimates that hundreds of millions of patients are affected by healthcare associated infections worldwide each year, with 7-10% of all hospitalized patients acquiring at least one health-care associated infection during their hospitalization. Viruses and bacteria can also readily pass through other public or semi-public spaces, such as airports, sports stadiums, museums, and hotels if care is not taken to manage pathogen transmission pathways.

Implementing robust and aggressive hygiene practices are the best way to protect against the acquisition and transmission of pathogens. The types of hygiene practices used will depend on the environment of operation but may include systematic handwashing, controlled food preparation techniques, systematic cleaning and sterilization of contact surfaces in the environment, and the like. While plans and practices can be established for managing hygiene activity in an environment, the lack of hygiene compliance surveillance systems makes tracking and controlling compliance challenging. The challenges associated with ensuring hygiene compliance are exacerbated by the fact that the employees assigned cleaning tasks are often entry-level positions, characterized by high turnover and, in some cases, limited motivation and dedication to performing the assigned tasks.

SUMMARY

In general, this disclosure is directed to devices, systems, and techniques for managing hygiene activity by deploying a computing device associated with an individual performing cleaning to track the efficacy of their cleaning actions. The computing device can include one or more sensors that detect and measure cleaning motion associated movement of the computing device caused by movement of the individual, e.g., during a cleaning event. In some examples, the computing device is worn by the individual performing the cleaning, such as at a location between their shoulder and tip of their fingers (e.g., wrist, upper arm). In either case, the computing device can detect movement associated with the individual going about their assigned tasks, which may include movement during cleaning activities as well as interstitial movements between cleaning activities. The movement data generated by the computing device can be analyzed to determine an efficacy of the cleaning being performed by the individual. In some configurations, an operation of the computing device is controlled based on the efficacy of the cleaning determined, causing the individual performing the cleaning to modify their cleaning activity in response to the operation. Additionally or alternatively, the efficacy of the cleaning determined can be stored for the cleaning event, providing cleaning validation information for the environment being cleaned.

The types of hygiene activities monitored during a cleaning event may vary depending on the hygiene practices established for the environment being cleaned. As one example, the individual performing cleaning may be assigned a certain number of target surfaces to be cleaned. For example, in the case of a healthcare environment, the surfaces to be cleaned may include a light switch, a table top, a bed rail, a door knob, a medication dispensing pole, a faucet handle, and the like. In the case of a food preparation environment (e.g., restaurant, catering facility), the surface may include food preparation counters, floor surfaces, a fryer, a grill, stove surfaces, microwave surfaces, refrigerator surfaces, and the like. In either case, the individual performing cleaning may be assigned a number of surfaces to be cleaned.

During operation, the computing device can generate a signal corresponding to movement of the device caused by the individual performing cleaning carrying out their tasks. Each surface targeted for cleaning may have a different movement signal associated with cleaning of that target surface. Movement data generated by the computing device can be compared with reference movement data associated with each target surface. If the movement data indicates that the individual performing cleaning has missed a target surface, the computing device may perform an operation. For example, the computing device may provide an alert in substantially real time instructing the user to complete cleaning of the missed target surface.

Additionally or alternatively, the quality of cleaning of any particular target surface may also be determined using movement data generated by the computing device during the cleaning operation. For example, the movement data generated by the computing device during cleaning of a particular surface can be compared with reference movement data associated with a quality of cleaning of that target surface. The reference movement data associated with the quality of cleaning may correspond to a thoroughness with which the target surface is cleaned and/or an extent or area of the target surface.

In some applications, the individual carrying the computing device may be tasked with performing cleaning and non-cleaning tasks and/or performing multiple different cleaning tasks. For example, a protocol for the individual may dictate that they clean one or more target surfaces in the environment then perform an individual hand sanitizing event on themselves before turning to other tasks. The computing device can generate a signal corresponding to movement during this entire course of activity. Movement data generated by the computing device can be compared with reference movement data to classify and distinguish between cleaning and non-cleaning actions. The movement data identified as corresponding to a cleaning action can further by analyzed to determine the specific type of cleaning action performed (e.g., surface cleaning as opposed to hand cleaning). In some examples, the quality of that specific cleaning action is further evaluated with reference to movement data associated with a quality of cleaning for that specific cleaning action. In this way, a total hygiene management system may be provided to monitor and/or control multiple different types of hygiene activity.

The addition of hygiene compliance surveillance and control, as described herein, can allow users of the technology to reduce incidents of pathogen transmission through ineffective or incomplete cleaning. For example, organizations that run food preparation environments can see reduced incidents of foodborne illness associated with their facility after deploying the technology as compared to before deploying the technology. As another example, healthcare organizations can see reduced incidents of health care-associated infections after deploying the technology as compared to before deploying the technology. Other environments and applications can also benefit from the technology.

In one example, a method of reducing illnesses and infections caused by ineffective cleaning through tracked cleaning efficacy is described. The method includes detecting, by a wearable computing device that is worn by an individual performing cleaning on a plurality of target surfaces, movement associated with the wearable device during a cleaning event. The method also involves determining, based on the movement associated with the wearable computing device, whether the individual has performed a cleaning operation on each of the plurality of target surfaces by at least comparing movement data generated by the wearable device with reference movement data associated with cleaning of each of the plurality of target surfaces. In addition, the method involves, responsive to determining that the individual has not performed the cleaning operation on at least one of the plurality of target surfaces, performing, by the wearable computing device, an operation.

In another example, a wearable computing device is described. The device includes at least one sensor configured to detect movement associated with the wearable computing device, at least one processor, and a memory comprising instructions that, when executed, cause at least one processor to perform certain actions. The example specifies that the actions include receiving, from the at least one sensor, movement data for the wearable computing device while an individual wearing the wearable computing device performs a cleaning operation on a plurality of target surfaces during a cleaning event. The actions also include determining, based on the movement data, whether the individual has performed the cleaning operation on each of the plurality of target surfaces by at least comparing movement data with reference movement data associated with cleaning of each of the plurality of target surfaces. The actions also involve, responsive to determining that the individual has not performed the cleaning operation on at least one of the plurality of target surfaces, performing an operation.

In another example, a method of establishing a customer-specific system for tracking cleaning efficacy is described. The method includes performing, by an individual wearing a wearable computing device, a cleaning operation on each of a plurality of target surfaces, the plurality of target surfaces being selected as target surfaces of which cleaning is desired to be tracked in connection with subsequent cleaning events. The method also includes generating, by the wearable computing device, movement data associated with movement of the wearable device during the cleaning operation performed on each of a plurality of target surfaces. The method further involves associating different portions of the movement data generated during the cleaning operation with a particular one of each of the plurality of target surfaces on which the individual has performed the cleaning operation. In addition, the method involves determining, for each of the plurality of different target surfaces, reference data indicative of the cleaning operation being performed from the associated different portion of movement data for each of the plurality of different target surfaces. The method further includes storing the reference data for each of the plurality of different target surfaces for use in connection with subsequent cleaning events.

In another example, a method of controlling cleaning effectiveness is described. The method includes detecting, by a wearable computing device that is worn by an individual performing cleaning on a target surface, movement associated with the wearable device during a cleaning event. The method also includes determining, based on the movement associated with the wearable computing device, a quality of cleaning for the target surface by at least comparing movement data generated by the wearable device with reference movement data associated with a threshold quality of cleaning for the target surface. The method further involves, responsive to determining that the target surface has not been effectively cleaned to the threshold quality of cleaning, performing, by the wearable computing device, an operation.

In another example, a wearable computing device is described. The device includes at least one sensor configured to detect movement associated with the wearable computing device, at least one processor, and a memory comprising instructions that, when executed, cause the at least one processor to perform certain actions. The actions include receiving, from the at least one sensor, movement data for the wearable computing device while an individual wearing the wearable computing device performs a cleaning operation on a target surface during a cleaning event. The actions also include determining, based on the movement data, a quality of cleaning for the target surface by at least comparing movement data with reference movement data associated with a threshold quality of cleaning for the target surface. The actions further include, responsive to determining that the target surface has not been effectively cleaned to the threshold quality of cleaning, performing an operation.

In another example, a method of total hygiene management is described. The method involves determining, based on movement of a wearable computing device, at least one feature of movement that indicates a wearer of the wearable computing device is performing a cleaning action, thereby distinguishing movement of the wearable computing device during non-cleaning actions. The method includes determining, based on comparison of the feature(s) of movement with reference to movement data associated with different types of cleaning actions, a specific type of cleaning action performed by the wearer of the wearable computing device. The method also includes determining a quality of cleaning for the specific type of cleaning action performed by at least comparing movement data generated by the wearable device during the specific type of cleaning action with reference movement data associated with a threshold quality of cleaning for the specific type of cleaning action. The method further includes, responsive to determining that the specific type of cleaning action performed by the wearer of the wearable computing device does not satisfy the threshold quality of cleaning, performing, by the wearable computing device, an operation.

In another example, a wearable computing device is described. The device includes at least one sensor configured to detect movement associated with the wearable computing device, at least one processor, and a memory comprising instructions that, when executed, cause the at least one processor to perform certain actions. The actions include receiving, from the at least one sensor, movement data associated with the wearable computing device, and determining, based on the movement data, at least one feature of movement that indicates the individual wearing the wearable computing device is performing a cleaning action, thereby distinguishing movement of the wearable computing device during non-cleaning actions. The actions further include determining, based on comparison of the feature of movement with reference to movement data associated with different types of cleaning actions, a specific type of cleaning action performed by the wearer of the wearable computing device. The actions also involve determining, a quality of cleaning for the specific type of cleaning action performed by at least comparing the movement data generated during the specific type of cleaning action to reference movement data associated with a threshold quality of cleaning for the specific type of cleaning action. The actions further include, responsive to determining that the specific type of cleaning action performed does not satisfy the threshold quality of cleaning, performing an operation.

The details of one or more examples are set forth in the accompanying drawings and the description below. Other features, objects, and advantages will be apparent from the description and drawings, and from the claims.

BRIEF DESCRIPTION OF DRAWINGS

FIGS. 3A-3C illustrate example surfaces and/or equipment that may be cleaned, optionally using example tools, the cleaning efficacy of which is evaluated according to the present disclosure.

FIG. 7 illustrates an example hand hygiene protocol that may be specified for a wearer of a wearable computing device.

FIGS. 17A-17D illustrate of an example sequential series of user interface graphics that may be displayed to a user to help guide execution of a cleaning protocol.

DETAILED DESCRIPTION

Figure 1:
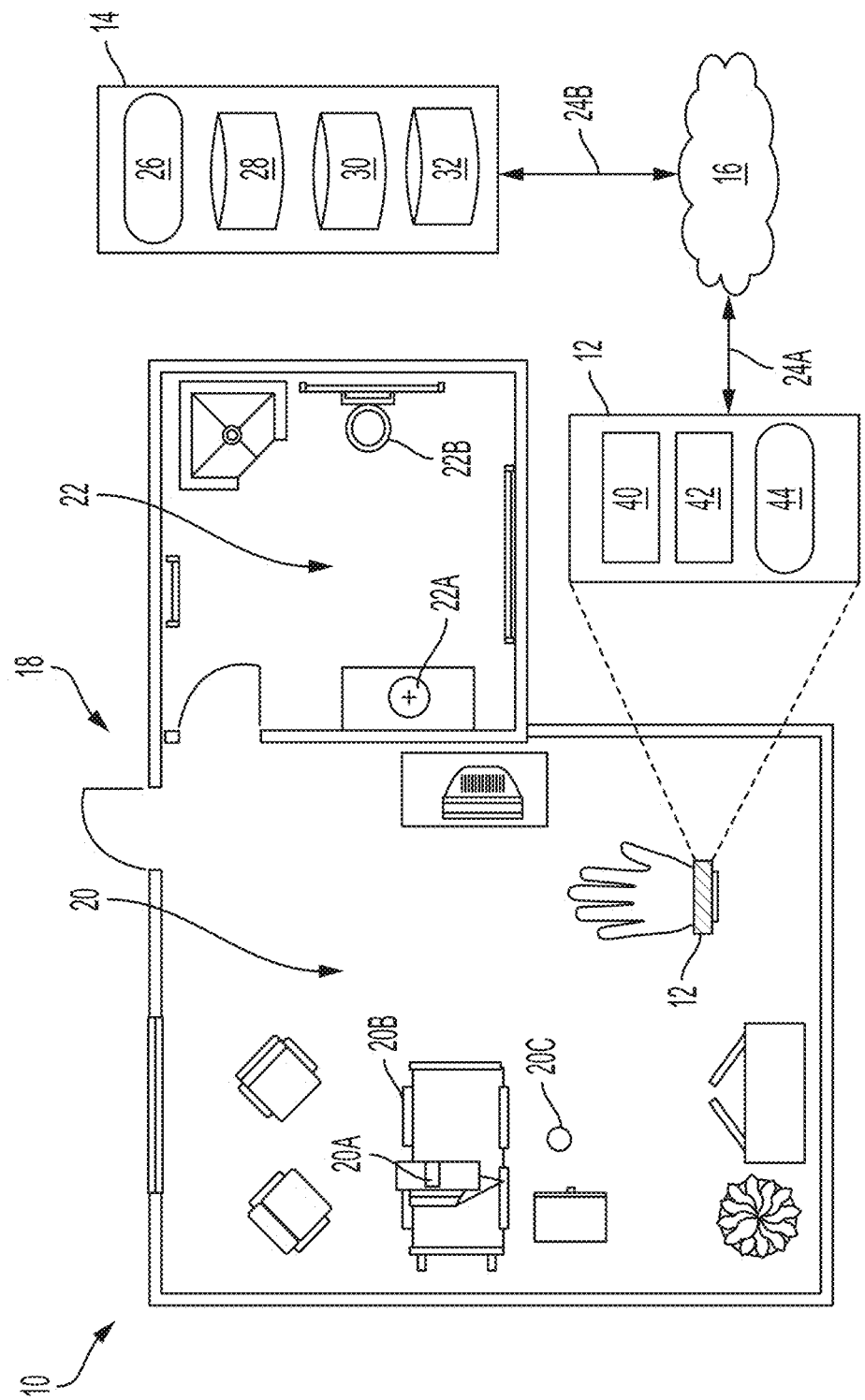
FIG. 1 is a conceptual diagram illustrating an example computing system that is configured to track cleaning efficacy of an individual performing cleaning during a cleaning event

In general, this disclosure is directed to devices, systems, and techniques utilizing a wearable computing device (e.g., an activity tracker, a computerized watch, etc.) to detect movement associate with an individual while performing one or more hygiene-related tasks. A computing system (e.g., a server, a mobile phone, etc.) may communicate with a wearable computing device (e.g., activity tracker, watch) via a network. The wearable computing device may, over time, detect movements (e.g., accelerations, angular velocity, changes in tilt, etc.) and may provide information about the detected movements (e.g., as movement data) to the computing system via the network. In some implementations, the computing system and/or wearable computing device may identify features of the movement data corresponding to specific hygiene activity being performed.

For example, the computing system may determine whether certain objects targeted for cleaning have, in fact, been cleaned, e.g., by comparing movement data associated with cleaning of each target object with reference movement data corresponding to cleaning of that object. As another example, the computing system may determine whether a particular object targeted for cleaning has been effectively cleaned, e.g., by comparing movement data associated with a level of cleaning of that target object with reference movement data corresponding to a threshold level of cleaning for the object.

As yet a further example, the computing system may distinguish different types of hygiene activities performed during a course of movement and evaluate hygiene compliance associated with one or more of those hygiene activities. For instance, the computing system may determine that a wearer of the computing device has performed a first type of cleaning action (e.g., floor surface cleaning, cleaning of the equipment) and a second type of cleaning action (e.g., cleaning of the wearer's hands). The computing system may determine a quality of one or both cleaning actions and/or an order in which the cleaning actions were performed. The computing system may further determine whether the quality of the cleaning action(s) and/or order of cleaning conforms to hygiene-compliance standards set for the environment in which the actions were performed.

In some implementations, the computing system generates and stores cleaning validation information associated with the environment in which one or more hygiene actions were performed. Unlike some cleaning compliance programs presently used that do not have an ability to surveil or validate that targeted cleaning actions were, in fact, performed, techniques according to the present disclosure may provide data-validated evidence of cleaning compliance. The cleaning compliance data may be stored information corresponding to one or more cleaning actions performed indicating, e.g., that certain surfaces and/or objects were cleaned during a cleaning event, a quality of cleaning of one or more surfaces and/or objects, and/or a type of cleaning action performed. The cleaning compliance data may also include a timestamp corresponding to when the cleaning action was performed and/or data corresponding to the actual cleaning movement performed during the cleaning action and/or other metadata corresponding to the context of measurement (e.g., room identification, GPS location). In this way, a cleaning provider can provide validation information evidencing the hygiene services performed and an owner or operator of a location can have evidence of hygiene compliance for their establishment.

In addition to or in lieu of providing cleaning validation information, a computing system according to the disclosure may invoke, or the wearable computing device may initiate, performance of an operation based on cleaning efficacy information determined based on movement data detected by the wearable cleaning device during a cleaning event. For example, the wearable cleaning device may activate a user alert feature and/or output information to an individual wearing the device indicating breach of a cleaning compliance standard. Such breach may indicate that the individual performing cleaning has missed a surface targeted for cleaning, not cleaned a target surface to a threshold level of cleaning quality, and/or performed a wrong sequence of cleaning actions (e.g., performed a hand hygiene cleaning action before an equipment cleaning action rather than vice versa). In some implementations, the wearable cleaning device may perform the operation to notify the wearer of the breach substantially in real time with the breach occurring. As a result, the wearer may take immediate corrective action to address the cleaning compliance breach. Additionally or alternatively, the operation performed by the wearable cleaning device may issue training to the wearer of the wearable cleaning device providing instructing to the user on corrective actions to be performed.

By providing cleaning compliance surveillance and control according to one or more aspects of the present disclosure, users of the technology may reduce incidents of pathogen transmission through ineffective or incomplete cleaning. For example, organizations that run food preparation environments can see reduced incidents of foodborne illness associated with their facility after deploying the technology as compared to before deploying the technology. As another example, healthcare organizations can see reduced incidents of health care-associated infections after deploying the technology as compared to before deploying the technology. Infection and/or illness rates attributed to ineffective cleaning may be reduced by at least 20% after deploying the technology as compared to prior to deploying the technology, such as at least 40%, at least 60%, at least 80%, or at least 90%.

Throughout the disclosure, examples are described where a computing system (e.g., a server, etc.) and/or computing device (e.g., a wearable computing device, etc.) may analyze information (e.g., accelerations, orientations, etc.) associated with the computing system and/or computing device. Such examples may be implemented so that the computing system and/or computing device can only perform the analyses after receiving permission from a user (e.g., a person wearing the wearable computing device) to analyze the information. For example, in situations discussed below in which the mobile computing device may collect or may make use of information associated with the user and the computing system and/or computing device, the user may be provided with an opportunity to provide input to control whether programs or features of the computing system and/or computing device can collect and make use of user information (e.g., information about a user's occupation, contacts, work hours, work history, training history, the user's preferences, and/or the user's past and current location), or to dictate whether and/or how to the computing system and/or computing device may receive content that may be relevant to the user. In addition, certain data may be treated in one or more ways before it is stored or used by the computing system and/or computing device, so that personally-identifiable information is removed. For example, a user's identity may be treated so that no personally identifiable information can be determined about the user, or a user's geographic location may be generalized where location information is obtained (such as to a city, ZIP code, or state level), so that a particular location of a user cannot be determined. Thus, the user may have control over how information is collected about the user and used by the computing system and/or computing device.

FIG. 1 is a conceptual diagram illustrating an example computing system 10, which is configured to track cleaning efficacy of an individual performing cleaning during a cleaning event. System 10 includes a wearable computing device 12, which can be worn by the individual performing cleaning and can generate data indicative of that individual's movement during the cleaning event, in accordance with one or more aspects of the present disclosure. System 10 also includes remote computing system 14 and network 16.

FIG. 1 shows wearable computing device 12 as being located within an environment 18 in which one or more hygiene actions (e.g., surface cleaning) may be performed. In the illustrated example, environment 18 is depicted as a healthcare environment having a bedroom 20 and a bathroom 22. Bedroom 20 may have one or more target surface intended to be cleaned during a cleaning event, such as a television remote control 20A, a bed rail 20B, and a medication support pole 20C, to name a few exemplary surfaces. Similarly, bathroom 22 may have one or more target surfaces intended to be cleaned during a cleaning event, such as a sink/faucet 22A and a toilet 22B, to again name a couple example surfaces. Such a healthcare environment may be susceptible to contraction of healthcare-acquired infections, making rigorous compliance with hygiene and cleaning protocols important for patient well-being. That being said, the techniques of the present disclosure are not limited to such an exemplary environment. Rather, the techniques of the disclosure may be utilized at any location where it is desirable to have validated evidence of hygiene compliance. Example environments in which aspects of the present disclosure may be utilized include, but are not limited to, a food preparation environment, a hotel-room environment, a food processing plant, and a dairy farm.

Wearable computing device 12 may be any type of computing device, which can be worn, held, or otherwise physically attached to a person, and which includes one or more processors configured to process and analyze indications of movement (e.g., sensor data) of the wearable computing device. Examples of wearable computing device 12 include, but are not limited to, a watch, an activity tracker, computerized eyewear, a computerized glove, computerized jewelry (e.g., a computerized ring), a mobile phone, or any other combination of hardware, software, and/or firmware that can be used to detect movement of a person who is wearing, holding, or otherwise being attached to wearable computing device 12. Such wearable computing device may be attached to a person's finger, wrist, arm, torso, or other bodily location sufficient to detect motion associated with the wearer's actions during the performance of a cleaning event. In some examples, wearable computing device 12 may have a housing attached to a band that is physically secured to (e.g., about) a portion of the wearer's body. In other examples, wearable computing device 12 may be insertable into a pocket of an article of clothing worn by the wearer without having a separate securing band physically attaching the wearable computing device to the wearer.

Although shown in FIG. 1 as a separate element apart from remote computing system 14, in some examples, some or all of the functionality of remote computing system 14 may be implemented by wearable computing device 12. For example, module 26 and data stores 28, 30, and 32 may exist locally at wearable computing device 12, to receive information regarding movement of the wearable computing device and to perform analyses as described herein. Accordingly, while certain functionalities are described herein as being performed by wearable computing device 12 and remote computing system 14, respectively, some or all of the functionalities may be shifted from the remote computing system to the wearable computing device, or vice versa, without departing from the scope of disclosure.

The phrase "cleaning action" as used herein refers to an act of cleaning having motion associated with it in multiple dimensions and which may or may not utilize a tool to perform the cleaning. Some examples of cleaning actions include an individual cleaning a specific object (e.g., door knob, toilet), optionally with a specific tool (e.g., rag, brush, mop), and an individual cleaning a portion of their body (e.g., washing hands). A cleaning action can include preparatory motion that occurs before delivery of a cleaning force, such as spraying a cleaner on a surface, wringing water from a mop, filling a bucket, soaking a rag, etc.

The term "substantially real time" as used herein means while an individual is still performing cleaning or is in sufficiently close temporal proximity to the termination of the cleaning that the individual is still in or proximate to the environment in which the cleaning occurred to perform a corrective cleaning operation.

The phrase "health care environment" as used herein in connection with a surface to be cleaned refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms as well as nursing and elderly care facilities. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

The phrase "food preparation environment" as used herein in connection with a surface to be cleaned refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Example food processing surfaces are found in ovens, fryers, grills, microwaves, refrigerators, countertops, storage receptacles, sinks, beverage chillers and warmers, meat chilling or scalding waters.

The phrase "cleaning operation" as used herein means the performance of a motion indicative of and corresponding to a cleaning motion. A cleaning motion can be one which an individual performs to aid in soil removal, pathogen population reduction, and combinations thereof.

The phrase "reference movement data" as used herein refers to both raw sensor data corresponding to the reference movement(s) and data derived from or based on the raw sensor data corresponding to the reference movement(s). In implementations where reference movement data is derived from or based on the raw sensor data, the reference movement data may provide a more compact representation of the raw sensor data. For example, reference movement data may be stored in the form of one or more window-granularity features, coefficients in a model, or other mathematical transformations of the raw reference data.

In FIG. 1, network 16 represents any public or private communication network. Wearable computing device 12 and remote computing system 14 may send and receive data across network 16 using any suitable communication techniques. For example, wearable computing device 12 may be operatively coupled to network 16 using network link 24A. Remote computing system 14 may be operatively coupled to network 16 by network link 24B. Network 16 may include network hubs, network switches, network routers, etc., that are operatively inter-coupled thereby providing for the exchange of information between wearable computing device 12 and remote computing system 14. In some examples, network links 24A and 24B may be Ethernet, Bluetooth, ATM or other network connections. Such connections may be wireless and/or wired connections.

Remote computing system 14 of system 10 represents any suitable mobile or stationary remote computing system, such as one or more desktop computers, laptop computers, mobile computers (e.g., mobile phone), mainframes, servers, cloud computing systems, etc. capable of sending and receiving information across network link 24B to network 16. In some examples, remote computing system 14 represents a cloud computing system that provides one or more services through network 16. One or more computing devices, such as wearable computing device 12, may access the one or more services provided by the cloud using remote computing system 14. For example, wearable computing device 12 may store and/or access data in the cloud using remote computing system 14. In some examples, some or all the functionality of remote computing system 14 exists in a mobile computing platform, such as a mobile phone, tablet computer, etc. that may or may not be at the same geographical location as wearable computing device 12. For instance, some or all the functionality of remote computing system 14 may, in some examples, reside in and be execute from within a mobile computing device that is in environment 18 with wearable computing device 12 and/or reside in and be implemented in the wearable device itself.

In some implementations, wearable computing device 12 can generate and store data indicative of movement for processing by remote computing system 14 even when the wearable computing device is not in communication with the remote computing system. In practice, for example, wearable computing device 12 may periodically lose connectivity with remote computing system 14 and/or network 16. In these and other situations, wearable computing device 12 may operate in an offline/disconnected state to perform the same functions or more limited functions the wearable computing device performs if online/connected with remote computing system 14. When connection is reestablished between computing device 12 and remote computing system 14, the computing device can forward the stored data generated during the period when the device was offline. In different examples, computing device 12 may reestablish connection with remote computing system 14 when wireless connectivity is reestablished via network 16 or when the computing device is connected to a docketing station to facilitate downloading of information temporarily stored on the computing device.

Remote computing system 14 in the example of FIG. 1 includes cleaning efficacy determination module 26 and one or more data stores, which is illustrated as including a target surfaces comparison data store 28, a cleaning quality comparison data store 30, and a cleaning action comparison data store 32. Cleaning efficacy determination module 26 may perform operations described using software, hardware, firmware, or a mixture of hardware, software, and firmware residing in and/or executing at remote computing system 14. Remote computing system 14 may execute cleaning efficacy determination module 26 with multiple processors or multiple devices. Remote computing system 14 may execute cleaning efficacy determination module 26 as a virtual machine executing on underlying hardware. Cleaning efficacy determination module 26 may execute as a service of an operating system or computing platform. Cleaning efficacy determination module 26 may execute as one or more executable programs at an application layer of a computing platform.

Features described as data stores can represent any suitable storage medium for storing actual, modeled, or otherwise derived data that cleaning efficacy determination module 26 may access to determine whether a wearer of wearable computing device 12 has performed compliant cleaning behavior. For example, the data stores may contain lookup tables, databases, charts, graphs, functions, equations, and the like that cleaning efficacy determination module 26 may access to evaluate data generated by wearable computing device 12. Cleaning efficacy determination module 26 may rely on features generated from the information contained in one or more data stores to determine whether sensor data obtained from wearable computing device 12 indicates that a person has performed certain cleaning compliance behaviors, such as cleaning all surfaces targeted for cleaning, cleaning one or more target surfaces appropriately thoroughly, and/or performing certain specific cleaning actions. The data stored in the data stores may be generated from and/or based on one or more training sessions, as described in greater detail with respect to FIGS. 4-6. Remote computing system 14 may provide access to the data stored at the data stores as a cloud-based service to devices connected to network 16, such as wearable computing device 12.

Cleaning efficacy determination module 26 may respond to requests for information (e.g., from wearable computing device 12) indicating whether an individual performing cleaning and wearing or having worn wearable computing device 12 has performed compliant cleaning activity. Cleaning efficacy determination module 26 may receive sensor data via link 24B and network 16 from wearable computing device 12 and compare the sensor data to one or more comparison data sets stored in data stores of the remote computing system 14. Cleaning efficacy determination module 26 may respond to the request by sending information from remote computing system 14 to wearable computing device 12 through network 16 via links.

Cleaning efficacy determination module 26 may be implemented to determine a number of different characteristics of cleaning behavior and compliance with cleaning protocols based on information detected by wearable computing device 12. In general, wearable computing device 12 may output, for transmission to remote computing system 14, information indicative of movement of the wearer (e.g., data indicative of a direction, location, orientation, position, elevation, etc. of wearable computing device 12), as discussed in greater detail below. Cleaning efficacy determination module 26 may discriminate movement associated with cleaning action from movement not associated with cleaning action during the cleaning event, or period over which movement data is captured, e.g., with reference to stored data in remote computing system 14. Cleaning efficacy determination module 26 may further analyze the movement data associated with cleaning action to determine whether such action is in compliance with one or more standards, e.g., based on comparative data stored in one or more data stores.

In one implementation, an individual performing cleaning may be assigned a schedule of multiple surfaces to be cleaned during a cleaning event. The schedule of surfaces to be cleaned may correspond to surfaces that are frequently touched by individuals in the environment and that are subject to contamination, or otherwise desired to be cleaned as part of a cleaning compliance protocol. The individual performing cleaning may be instructed on which surfaces should be cleaned during a cleaning event and, optionally, and order in which the surfaces should be cleaned and/or a thoroughness with which each surface should be cleaned.

During performance of the cleaning event, wearable computing device 12 may output information corresponding to movement of the wearable computing device. Cleaning efficacy determination module 26 may receive movement data from wearable computing device 12 and analyze the movement data with reference to target surface comparative data stored at data store 28. Target surface comparative data store 28 may contain data corresponding to cleaning for each of the target surfaces scheduled by the individual performing cleaning to be cleaned.

In some examples, cleaning efficacy determination module 26 determines one or more features of the movement data corresponding to cleaning of a particular surface. Each surface targeted for cleaning may have dimensions and/or an orientation within three-dimensional space unique to that target surface and which distinguishes it from each other target surface intended to be cleaned. Accordingly, movement associated with cleaning of each target surface may provide a unique signature, or comparative data set, that distinguishes movement associated with cleaning of each target surface within the data set. The specific features of the data defining the target surface may vary, e.g., depending on the characteristics of the target surface and characteristics of sensor data generated by wearable computing device 12. Target surface comparative data store 28 may contain data corresponding to cleaning of each target surface intended to be cleaned. For example, target surface comparative data store 28 may contain features generated from reference movement data associated with cleaning of each of the multiple target surfaces scheduled to be cleaned.

Cleaning efficacy determination module 26 can analyze one or more features of movement data generated during a cleaning event relative to the features in target surface comparative data store 28 to determine which of the target surfaces the individual has performed a cleaning on. Cleaning efficacy determination module 26 can determine if one or more target surfaces scheduled to be cleaned were cleaned or were not, in fact, cleaned based on reference to target surface comparison data store 28. Remote computing system 14 may communicate with wearable computing device 12 to initiate an operation via the wearable computing device in the event that at least one target surface scheduled to be cleaned was determined to not have been cleaned during the cleaning event.

As another implementation, an individual performing cleaning may be instructed on a quality with which a target surface should be cleaned during a cleaning event. The quality of cleaning may be instructed through a cleaning protocol training the individual on how to properly clean the target surface. Example characteristics of the cleaning protocol may specify a technique to be used to clean the target surface, an amount of force to be applied via a cleaning implement when cleaning the target surface, an extent or area of the target surface to be cleaned, and/or a duration of cleaning that should be performed on the target surface.

In some examples, a cleaning protocol may specify a sequence of one or more activities to be performed and/or a particular cleaning technique or series of techniques to be used when performing the one or more cleaning activities. Example cleaning activities that may be specified as part of a cleaning protocol include an order of surfaces to be cleaned (e.g., cleaning room from top-to-bottom, wet-to-dry, and/or least-to-most soiled). Example cleaning techniques that may be specified include a specific type of cleaning to be used on a particular surface (e.g., a scrubbing action, using overlapping strokes) and/or a sequential series of cleaning steps to be performed on the particular surface (e.g., removing visible soils followed by disinfection).

During performance of a cleaning event, wearable computing device 12 can output information corresponding to movement of the wearable computing device. Cleaning efficacy determination module 26 may receive movement data from wearable computing device 12 and analyze the movement data with reference to cleaning quality comparative data stored at data store 30. Cleaning quality comparative data store 30 may contain data corresponding to a quality of cleaning for the target surface intended to be cleaned by the individual performing clean.

In some examples, cleaning efficacy determination module 26 determines one or more features of the movement data corresponding to quality of cleaning of a surface. The movement data may be indicative of amount of work, or intensity, of the cleaning action performed. Additionally or alternatively, the movement data may be indicative of an area of the surface being cleaned (e.g., dimensions and orientation in three-dimensional space), which may indicate whether the individual performing cleaning has cleaned an entirety of the target surface. Still further additionally or alternatively, the movement data may be indicative of the type of cleaning technique, or series of different cleaning techniques, performed on the surface. The specific features of the data defining the quality of cleaning may vary, e.g., depending on the characteristics of the cleaning protocol dictating the quality cleaning, the characteristics of the surface being cleaned, and/or the characteristics of the sensor data generated by wearable computing device 12.

Cleaning quality comparison data store 30 may contain data corresponding to the quality of cleaning of each surface, the quality of cleaning of which is intended to be evaluated. Cleaning quality comparison data store 30 may contain features generated from reference movement data associated with a compliant quality of cleaning for each surface, the quality of cleaning of which is intended to be evaluated. The reference movement data may correspond to a threshold level of cleaning indicated by the originator of the reference movement data as corresponding to a suitable or compliant level of quality.

Cleaning efficacy determination module 26 can analyze one or more features of movement data generated during a cleaning event relative to features in cleaning quality comparison data store 30 to determine whether the surface on which the individual performed cleaning has been cleaned to a threshold level of quality. Cleaning efficacy determination module 26 can determine if a target surface was cleaned to a threshold level of quality or if the surface was not cleaned to the threshold level of quality based on reference to cleaning quality comparison data store 30. Remote computing system 14 may communicate with wearable computing device 12 to initiate an operation via the wearable computing device in the event that a target surface was determined to not have been cleaned to the threshold level of quality.

As another example implementation, an individual performing cleaning may be assigned multiple cleaning actions to be performed as part of a protocol of work. Each specific type of cleaning action may be different than each other specific type of cleaning action and, in some examples, may desirably be performed in a specified order. For example, one type of cleaning action that may be performed is an environmental cleaning action in which one or more surfaces in environment 18 are desired to be cleaned. Examples of these types of cleaning actions include floor surface cleaning actions (e.g., sweeping, mopping) and non-floor surface cleaning actions (e.g., cleaning equipment within an environment 18). Another type of cleaning action that may be performed is a personal cleaning action, such as a hand hygiene cleaning event in which an individual conducts a handwashing protocol (e.g., with an alcohol-containing sanitizer, with soap and water). As part of a total hygiene management program, the efficacy and/or order of each of the different types of cleaning actions performed the individual may be evaluated.

For example, wearable computing device 12 may output information corresponding to movement of the wearable computing device during a period of time in which the wearer performs multiple cleaning actions as well as non-cleaning actions. Cleaning efficacy determination module 26 may receive movement data from wearable computing device 12 and analyze the movement data with reference to cleaning action comparison data store 32. Cleaning action comparison data store 32 may contain data corresponding to multiple different types of cleaning actions that may be performed by an individual wearing wearable computing device 12. Each type of cleaning action may have a movement signature associated with it that is stored in cleaning action comparison data store 32.

Cleaning efficacy determination module 26 may distinguish movement data associated with cleaning actions from movement data associated with non-cleaning actions with reference to cleaning action comparison data store 32. Cleaning efficacy determination module 26 may further determine a specific type of cleaning action(s) performed by the wearer of wearable computing device 12 with reference to cleaning action comparison data store 32. In some implementations, cleaning efficacy determination module 26 may further determine a quality of clean for one or more of the specific types of cleaning actions performed by the ware with further reference to cleaning quality comparison data store 30.

In some examples, cleaning efficacy determination module 26 determines one or more features of the movement data corresponding to the multiple cleaning actions performed by the wearer. Each cleaning action may have movement data associated with it that distinguishes it from each other type of cleaning action. Accordingly, movement data generated during the performance of multiple cleaning actions can allow each specific cleaning action to be distinguished from each other specific cleaning action. The specific features of the data defining a specific cleaning action may vary, e.g., depending on the type of cleaning action performed and the characteristics of the sensor data generated by wearable computing device 12. Cleaning action comparison data store 32 may contain data distinguishing cleaning movement from non-cleaning movement. Cleaning action comparison data store 32 may further contain data corresponding to each type of cleaning action, the compliance of which is intended to be evaluated. For example, cleaning action compliance data store 32 may contain features generated from reference movement data associated with each type of cleaning action that may be determined from movement data.

Cleaning efficacy determination module 26 can analyze one or more features of movement generated during the course of movement relative to the features defining different cleaning actions. For example, cleaning efficacy determination module 26 can analyze one or more features of movement data generated during the duration of movement (e.g., cleaning event) to distinguish periods of movement corresponding to cleaning action from periods of movement corresponding to non-cleaning actions, e.g., with reference to cleaning action compliance data store 32. Additionally or alternatively, cleaning efficacy determination module 26 can analyze one or more features of movement corresponding to periods of cleaning to determine specific types of cleaning actions performed during each period of cleaning, e.g., with reference to cleaning action compliance data store 32. Cleaning action compliance data store 32 may further determine whether one or more of the specific types of cleaning actions performed were performed with a threshold level of quality, e.g., with reference to clean quality comparison data store 30.

In some examples, cleaning efficacy determination module 26 can analyze one or more features of movement data generated during the duration of movement to distinguish periods of movement corresponding to cleaning action from periods of movement corresponding to non-cleaning actions, e.g., with reference to cleaning action compliance data store 32. Cleaning efficacy determination module 26 can further analyze the one or more features of movement data, e.g., with reference to cleaning action compliance data store 32, to determine whether a specified order of cleaning was performed (e.g., cleaning room from top-to-bottom, wet-to-dry, and/or least-to-most soiled). Additionally or alternatively, cleaning efficacy determination module 26 can further analyze the one or more features of movement data, e.g., with reference to cleaning action compliance data store 32, to determine whether a particular surface has been cleaned used a specified technique or specified series of techniques (e.g., a scrubbing action, using overlapping strokes, removing visible soils followed by disinfection).

Remote computing system 14 may communicate with wearable computing device 12 to initiate an operation via the wearable computing device in the event that the cleaning activity performed does not comply with protocol standards, such as a specific type of cleaning action expected to be performed having not been performed and/or a specific type of cleaning action having been performed to less than a threshold level of cleaning quality.

In some examples, wearable computing device 12 may output, for transmission to remote computing system 6, information comprising an indication of movement (e.g., data indicative of a direction, speed, location, orientation, position, elevation, etc.) of wearable computing device 12. Responsive to outputting the information comprising the indication of movement, wearable computing device 12 may receive, from remote computing system 14, information concerning an efficacy of cleaning that is being performed or has been performed. The information may indicate that the individual performing cleaning and wearing wearable computing device 12 has performed a cleaning operation on all surfaces targeted for cleaning or, conversely, has not performed a cleaning operation on at least one surface targeted for cleaning. Additionally or alternatively, the information may indicate that the individual performing cleaning and wearing wearable computing device 12 has performed cleaning to a threshold level of quality or, conversely, has not performed cleaning to a threshold level of quality. As still a further example, the information may indicate that the individual performing cleaning and wearing wearable computing device 12 has not performed a specific type of cleaning action expected to be performed as part of a stored cleaning protocol and/or the individual has performed the specific type of cleaning action but has not performed it to the threshold level of quality and/or in the wrong order.

In the example of FIG. 1, wearable computing device 12 is illustrated as a wrist-mounted device, such as a watch or activity tracker. Wearable computing device 12 can be implemented using a variety of different hardware devices, as discussed above. Independent of the specific type of device used as wearable computing device 12, the device may be configured with a variety of features and functionalities.

In the example of FIG. 1, wearable computing device 12 is illustrated as including a user interface 40. User interface 40 of wearable computing device 12 may function as an input device for wearable computing device 12 and as an output device. User interface 40 may be implemented using various technologies. For instance, user interface 40 may function as an input device using a microphone and as an output device using a speaker to provide an audio-based user interface. User interface 40 may function as an input device using a presence-sensitive input display, such as a resistive touchscreen, a surface acoustic wave touchscreen, a capacitive touchscreen, a projective capacitance touchscreen, a pressure sensitive screen, an acoustic pulse recognition touchscreen, or another presence-sensitive display technology. User interface 40 may function as an output (e.g., display) device using any one or more display devices, such as a liquid crystal display (LCD), dot matrix display, light emitting diode (LED) display, organic light-emitting diode (OLED) display, e-ink, or similar monochrome or color display capable of outputting visible information to the user of wearable computing device 12.

User interface 40 of wearable computing device 12 may include physically-depressible buttons and/or a presence-sensitive display that may receive tactile input from a user of wearable computing device 12. User interface 40 may receive indications of the tactile input by detecting one or more gestures from a user of wearable computing device 12 (e.g., the user touching or pointing to one or more locations of user interface 40 with a finger or a stylus pen). User interface 40 may present output to a user, for instance at a presence-sensitive display. User interface 40 may present the output as a graphical user interface which may be associated with functionality provided by wearable computing device 12. For example, user interface 40 may present various user interfaces of applications executing at or accessible by wearable computing device 12 (e.g., an electronic message application, an Internet browser application, etc.). A user may interact with a respective user interface of an application to cause wearable computing device 12 to perform operations relating to a function. Additionally or alternatively, user interface 40 may present tactile feedback, e.g., through a haptic generator.

FIG. 1 shows that wearable computing device 12 includes one or more sensor devices 42 (also referred to herein as "sensor 42") for generating data corresponding to movement of the device in three-dimensional space. Many examples of sensor devices 42 exist including microphones, cameras, accelerometers, gyroscopes, magnetometers, thermometers, galvanic skin response sensors, pressure sensors, barometers, ambient light sensors, heart rate monitors, altimeters, and the like. In some examples, wearable computing device 12 may include a global positioning system (GPS) radio for receiving GPS signals (e.g., from a GPS satellite) having location and sensor data corresponding to the current location of wearable computing device 12 as part of the one or more sensor devices 42. Sensor 42 may generate data indicative of movement of wearable computing device in one or more dimensions and output the movement data to one or more modules of wearable computing device 12, such as module 44. In some implementations, sensor device 42 is implemented using a 3-axis accelerometer. Additionally or alternatively, sensor device 42 may be implemented using a 3-axis gyroscope.

Wearable computing device 12 may include a user interface module 44 and, optionally, additional modules (e.g., cleaning efficacy determination module 26). Each module may perform operations described using software, hardware, firmware, or a mixture of hardware, software, and firmware residing in and/or executing at wearable computing device 12. Wearable computing device 12 may execute each module with one or multiple processors. Wearable computing device 12 may execute each module as a virtual machine executing on underlying hardware. Each module may execute as one or more services of an operating system and/or a computing platform. Each module may execute as one or more remote computing services, such as one or more services provided by a cloud and/or cluster-based computing system. Each module may execute as one or more executable programs at an application layer of a computing platform.

User interface module 44 may function as a main control module of wearable computing device 12 by not only providing user interface functionality associated with wearable computing device 12, but also by acting as an intermediary between other modules (e.g., module 46) of wearable computing device 12 and other components (e.g., user interface 40, sensor device 42), as well as remote computing system 14 and/or network 16. By acting as an intermediary or control module on behalf of wearable computing device 12, user interface module 44 may ensure that wearable computing device 12 provides stable and expected functionality to a user. User interface module 44 may rely on machine learning or other type of rules based or probabilistic artificial intelligence techniques to control how wearable computing device 12 operates.

User interface module 44 may cause user interface 40 to perform one or more operations, e.g., in response to one or more cleaning determinations made by cleaning efficacy determination module 26. For example, user interface module 44 may cause user interface 40 to present audio (e.g., sounds), graphics, or other types of output (e.g., haptic feedback, etc.) associated with a user interface. The output may be responsive to one or more cleaning determinations made and, in some examples, may provide cleaning information to the wearer of wearable computing device 12 to correct cleaning behavior determined to be noncompliant.

For example, user interface module 44 may receive information via network 16 from cleaning efficacy determination module 26 that causes user interface module 44 to control user interface 40 to output information to the wearer of wearable computing device 12. For instance, when cleaning efficacy determination module 26 determines whether or not the user has performed certain compliant cleaning behavior (e.g., performed a cleaning operation on each surface targeted for cleaning, cleaned a target surface to a threshold quality of cleaning, and/or performed a specific type of cleaning action and/or perform such action to a threshold quality of cleaning), user interface module 44 may receive information via network 16 corresponding to the determination made by cleaning efficacy determination module 26. Responsive to determining that wearable computing device 12 has or has not performed certain compliant cleaning behavior, user interface module 44 may control wearable computing device 12 to perform an operation, examples of which are discussed in greater detail below.

Cleaning efficacy information determined by system 10 may be used in a variety of different ways. As noted, the cleaning efficacy information can be stored for a cleaning event, providing cleaning validation information for the environment being cleaned. Additionally or alternatively, the cleaning efficacy information can be communicated to a scheduling module, e.g., executing on system 10 or another computing system, which schedules the availability of certain resources in the environment in which the cleaning operation is being performed. In a healthcare environment, for example, the scheduling module may determine the availability of a room (e.g., patient room, surgical room) and schedule patient assignments/procedures for the room based on when the room is turned over from a prior use (e.g., cleaned) and available. As another example, the scheduling module may determine the availability of equipment for use based on when the equipment is turned over from a prior use (e.g., cleaned) and available. Cleaning efficacy information determined by system 10 can be communicated to the scheduling module to determine when a resource (e.g., room, equipment) is projected to be cleaned and/or cleaning is complete. For example, the scheduling module may determine that a resource is projected to be available in a certain period of time (e.g., X minutes) based on substantially real-time cleaning efficacy and progress information generated by system 10. The scheduling module can then schedule a subsequent use of the resource based on this information.

As another example, cleaning efficacy information determined by system 10 may be used to train and/or incentivize a cleaner using the system. Computing system 10 may include or communicate with an incentive system that issues one or more incentives to a cleaner using the system based on cleaning performance monitored by wearable computing device 12. The incentive system may issue a commendation (e.g., an encouraging message issued via user interface 40 and/or via e-mail and/or textual message) and/or rewards (e.g., monetary rewards, prizes) in response to an individual user meeting one or more goals (e.g., efficiency goals, quality goals) as determined based on motion data generated by the wearable computing device worn by the user.

Figure 2:
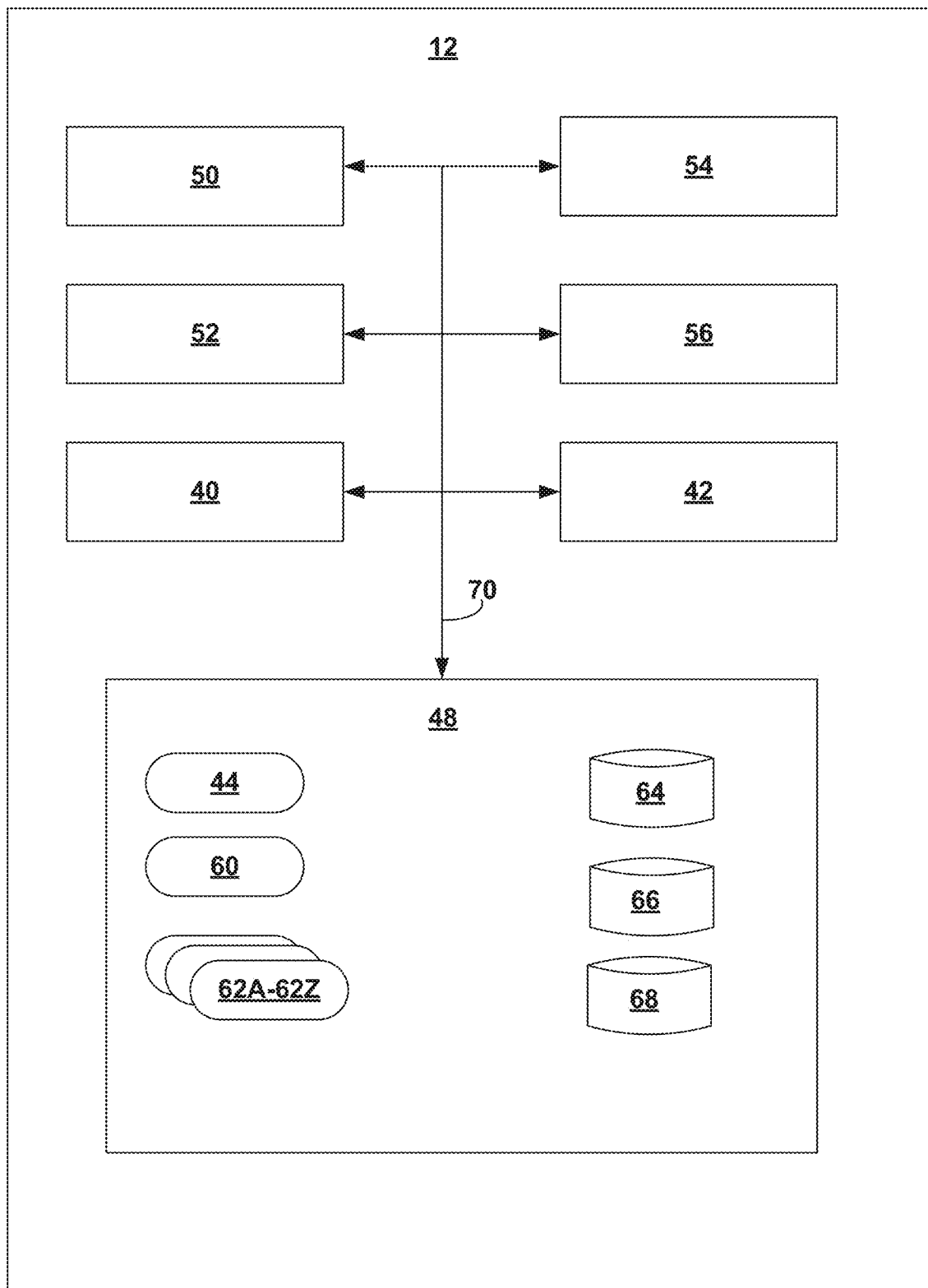
FIG. 2 is a block diagram illustrating an example wearable computing device configured according to one or more aspects of the present disclosure.

FIG. 2 is a block diagram illustrating an example wearable computing device configured according to one or more aspects of the present disclosure. For example, the wearable computing device of FIG. 2 can be configured to determine whether or not a wearer of the device has performed certain compliant cleaning behavior (e.g., performed a cleaning operation on each surface targeted for cleaning, cleaned a target surface to a threshold quality of cleaning, and/or performed a specific type of cleaning action and/or performed such action to a threshold quality of cleaning and/or in a target cleaning order). Wearable computing device 12 of FIG. 2 is described below within the context of system 10 of FIG. 1. FIG. 2 illustrates only one particular example of wearable computing device 12 of system 10, and many other examples of wearable computing device 12 may be used in other instances and may include a subset of the components, additional components, or different components than those included in the example wearable computing device 12 shown in FIG. 2.

As shown in the example of FIG. 2, wearable computing device 12 includes user interface 40, sensor device 42, one or more processors 50, one or more input devices 52, one or more communication units 54, one or more output devices 56, and one or more storage devices 58. Storage devices 48 of wearable computing device 12 also include user interface module 44, cleaning efficacy determination module 60, application modules 62A-62Z (collectively referred to as, "application modules 62"), and data stores 64, 66, and 68.

Cleaning efficacy determination module 60 may generally correspond to cleaning efficacy determination module 26 of remote computing system 14 of system 10. Data stores 64, 66, and 68 may correspond, respectively, to data stores 28, 30, and 32 of remote computing system 14 of FIG. 1. Accordingly, functions described as being performed by or on remote computing system 14 (in combination with functions performed on wearable computing device 12) may be performed solely on wearable computing device 12 and/or processing tasks may otherwise be shifted from remote computing system 14 to wearable computing device 12.

Communication channels 70 may interconnect each of the components of wearable computing device 12 for inter-component communications (physically, communicatively, and/or operatively). In some examples, communication channels 70 may include a system bus, a network connection, an inter-process communication data structure, or any other method for communicating data.

One or more input devices 52 of wearable computing device 12 may receive input. Examples of input are tactile, audio, and video input. Input devices 52 of wearable computing device 12, in one example, includes a presence-sensitive display, touch-sensitive screen, mouse, keyboard, voice responsive system, video camera, microphone or any other type of device for detecting input from a human or machine. One or more output devices 56 of wearable computing device 12 may generate output. Examples of output are tactile, audio, and video output. Output devices 56 of wearable computing device 12, in one example, includes a haptic generator that provides tactile feedback to the wearer.

One or more communication units 54 of wearable computing device 12 may communicate with external devices (e.g., remote computing system 14) via one or more networks by transmitting and/or receiving network signals on the one or more networks. For example, wearable computing device 12 may use communication unit 54 to send and receive data to and from remote computing system 14 of FIG. 1. Wearable computing device 12 may use communication unit 54 to transmit and/or receive radio signals on a radio network such as a cellular radio network. Likewise, communication units 54 may transmit and/or receive satellite signals on a satellite network such as a global positioning system (GPS) network. Examples of communication unit 54 include a network interface card (e.g. such as an Ethernet card), an optical transceiver, a radio frequency transceiver, a GPS receiver, or any other type of device that can send and/or receive information. Other examples of communication units 54 may include short wave radios, cellular data radios, wireless Ethernet network radios, as well as universal serial bus (USB) controllers.

In some examples, user interface 40 of wearable computing device 12 may include functionality of input devices 52 and/or output devices 56. While illustrated as an internal component of wearable computing device 12, user interface 40 also represents and external component that shares a data path with wearable computing device 12 for transmitting and/or receiving input and output. For instance, in one example, user interface 40 represents a built-in component of wearable computing device 12 located within and physically connected to the external packaging of wearable computing device 12 (e.g., a screen on a mobile phone). In another example, user interface 40 represents an external component of wearable computing device 12 located outside and physically separated from the packaging of wearable computing device 12 (e.g., a device that shares a wired and/or wireless data path with the other components of wearable computing device 12).

One or more storage devices 64-68 within wearable computing device 12 may store information for processing during operation of wearable computing device 12 (e.g., wearable computing device 12 may store target surface comparison data 64 corresponding to data store 28 in FIG. 1), cleaning quality comparison data 66 (corresponding to data store 30 in FIG. 1), and/or cleaning action comparison data 68 (corresponding to data store 32 in FIG. 1). Such data may be accessed by other modules and features of wearable computing device 12 during execution at wearable computing device 12. In some examples, storage device 58 is a temporary memory, meaning that a primary purpose of storage device 58 is not long-term storage. Storage devices 58 on wearable computing device 12 may be configured for short-term storage of information as volatile memory and therefore not retain stored contents if powered off. Examples of volatile memories include random access memories (RAM), dynamic random access memories (DRAM), static random access memories (SRAM), and other forms of volatile memories known in the art.

Storage devices 58, in some examples, also include one or more computer-readable storage media. Storage devices 58 may be configured to store larger amounts of information than volatile memory. Storage devices 58 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Storage devices 58 may store program instructions and/or data for performing the features and functions described herein as being performed by any module, device, and/or system.

One or more processors 50 may implement functionality and/or execute instructions within wearable computing device 12. For example, processors 50 on wearable computing device 12 may receive and execute instructions stored by storage devices 58 that execute the functionality of user interface module 44, cleaning efficacy determination module 60, and application modules 62. These instructions executed by processors 50 may cause wearable computing device 12 to store information, within storage devices 58 during program execution. Processors 50 may execute instructions of modules (e.g., 44, 60, 62) to cause wearable computing device 12 to determine compliance with one or more characteristics of cleaning and, in some examples, control execution of an operation in response to determining one or more non-compliant behaviors. For example, processors 50 may execute instructions that cause user interface 40 to output at least one of an audible type alert, a visual type alert, and/or a haptic feedback type alert. Such one or more alerts may provide information indicating non-compliance with a cleaning protocol (e.g., failure to clean all surfaces targeted for cleaning, failure to clean a particular surface to a threshold cleaning quality), instruct the user on behavior to correct the non-compliance, specify details of the non-compliant activity (e.g., identify the missed target surface(s)), and/or otherwise inform the user of that the cleaning performed did not satisfy compliance standards.

Application modules 62 may include any additional type of application that wearable computing device 12 may execute. Application modules 62 may be stand-alone applications or processes. In some examples, applications modules 62 represent an operating system or computing platform of wearable computing device 12 for executing or controlling features and operations performed by other applications.

A variety of different surfaces and objects may be cleaned utilizing one or more aspects of the present disclosure. Examples of such surfaces are discussed in greater detail below in connection with FIG. 4. In some examples, one or more surfaces on which cleaning is performed are located in a healthcare environment, as discussed in connection with FIG. 1. In other examples, one or more surfaces on which cleaning is performed are located in a food preparation environment. FIGS. 3A-3C illustrate example surfaces and/or equipment that may be cleaned, optionally using example tools, the cleaning efficacy of which is evaluated according to the present disclosure. FIG. 3A illustrates an example floor cleaning protocol that may be specified for a wearer of wearable computing device 12 to follow. FIG. 3B illustrates an example grill cleaning protocol that may be specified for a wearer of wearable computing device 12 to follow. FIG. 3C illustrates an example fryer cleaning protocol that may be specified for a wearer of wearable computing device 12 to follow.

To make one or more cleaning efficacy determinations using wearable computing device 12, one or more calibration process may be performed to generate comparison data stored in data stores for reference during a subsequent cleaning event. For example, a supervised process may be used in which the individual that will wear the wearable computing device during subsequent cleaning activity goes through a calibration process using the device, or an analogue thereof (e.g., a device generating equivalent movement data to that generated by wearable computing device 12). Alternatively, a global, non-user-specific training may be performed to generate comparison data that is subsequently referenced during use of wearable computing device, which may help remove any need for user-specific calibration, but which may be less accurate. Thus, in some implementations, reference movement data stored in a data store (e.g., in wearable computing device 12 and/or remote computing system 14) is generated from movement data obtained during one or more training episodes in which one or more trainers (different that the individual subsequently performing cleaning) performs a cleaning operation (e.g., on each of a plurality of target surfaces or equivalents thereof) while wearing wearable computing device 12 or an equivalent thereof. In other implementations, reference movement data stored in a data store is generated from movement data obtained during one or more training episodes in which the actual individual performing the subsequent cleaning operation (e.g., on each of the plurality of target surfaces or equivalents thereof) wears wearable computing device 12 or an equivalent thereof.

Independent of how comparison data is generated, computing system 10 may be used to generate and/or store comparison data associated with different surfaces and/or areas to be cleaned and/or different levels of cleaning (e.g., different cleaning protocols) to be performed on those surfaces and/or areas. In some examples, a user may provide a user input to computing system 10 indicating that wearable computing device 12 is to be reassigned to monitor cleaning of one or more different surface(s), room(s), and/or areas than the wearable computing device was previously used to monitor. Alternatively, computing system 10 may automatically determine that the wearable computing device 12 has been reassigned based on motion data generated by the wearable computing device. In either case, computing system 10 may reset the context of measurement and/or the comparison data against which motion data generated by wearable computing device 12 is compared during subsequent operation. Additionally or alternatively, computing system 10 may change the level of cleaning to be performed and/or the protocol against which cleaning data is compared (e.g., such as when a hospital room is switched from a daily maintenance cleaning to a more thorough discharge cleaning).

Figure 4:
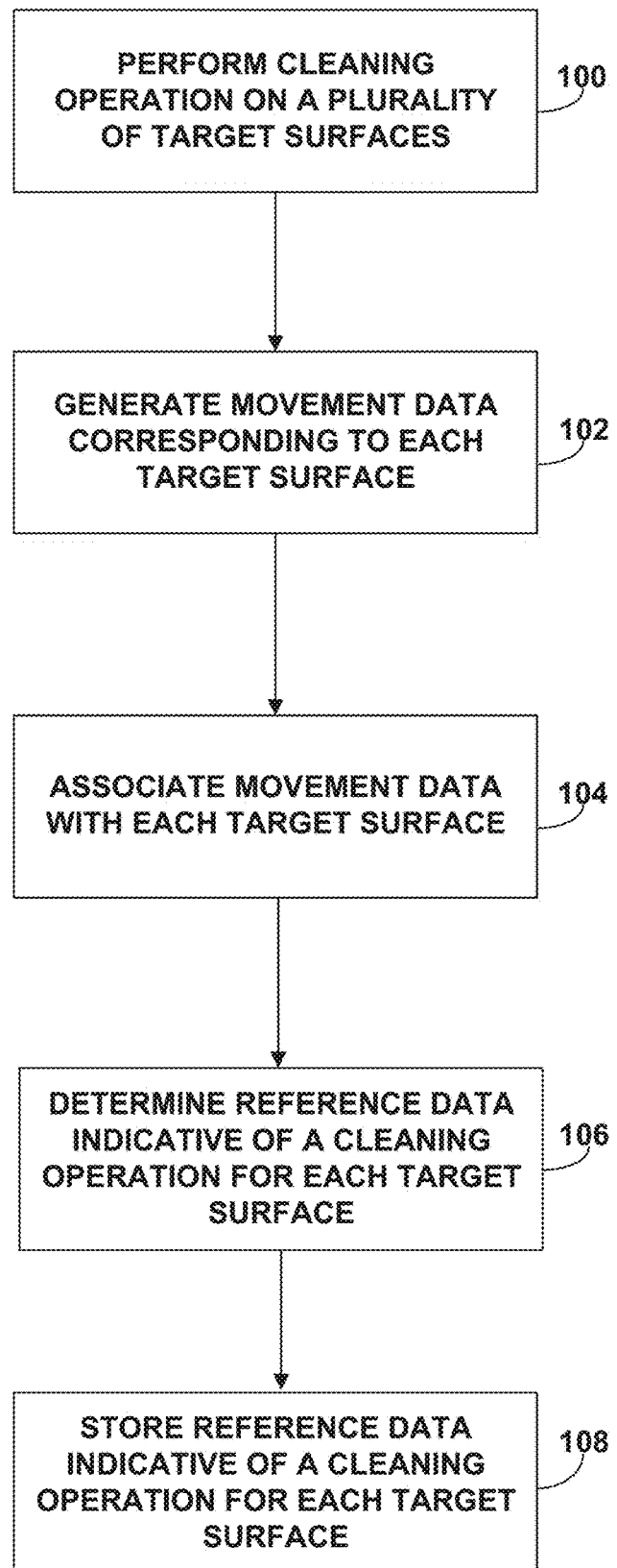
FIG. 4 is a flow diagram illustrating an example process for training an example wearable computing device to subsequently determine whether an individual performing cleaning has cleaned each of a plurality of target surfaces intended to be clean as part of an established protocol

FIG. 4 is a flow diagram illustrating an example process for training an example wearable computing device to subsequently determine whether an individual performing cleaning has cleaned each of a plurality of target surfaces intended to be clean as part of an established protocol. The process shown in FIG. 4 may be performed by one or more processors of a computing device, such as wearable computing device 12 illustrated in FIGS. 1 and 2. For purposes of illustration, FIG. 4 is described below within the context of computing system 10 of FIG. 1. It should be appreciated that the process of FIG. 4 may be performed by the individual who will be wearing wearable computing device 12 during subsequent cleaning or may be performed by a different individual (e.g., a trainer) other than the individual who will be performing the subsequently cleaning. In some examples, the process of FIG. 4 is performed by a single individual, while in other implementations, multiple different individuals perform the process to generate an aggregate data set corresponding to a broader population of users. For example, the generation of reference movement data according to any of the techniques described herein may be performed by: (1) a single individual in a single session, (2) multiple individuals in a single session for each, (3) a single individual across multiple sessions, and/or (4) multiple individuals each across multiple sessions.

In the example of FIG. 4, an individual wearing wearable computing device 12 performs a cleaning operation on each of a plurality of target surfaces (100). The plurality of target surfaces may be at least two surfaces, such as at least five surfaces, or at least ten surfaces, or at least fifteen surfaces. In some implementations, each target surface is a target object. Accordingly, description of performing a cleaning operation on a target surface may be implemented by performing such cleaning operation on a target object. Each target object may have boundaries in three-dimensional space that define an extent of the object to be cleaned. The boundaries of each target object may be different than each other target object intended to be cleaned, such that the cleaning operation performed for each target object results in a different movement than the cleaning operation performed for each other target object.

Each cleaning operation may be a movement action corresponding to cleaning of the target surface or object, optionally along with pre-cleaning preparatory motion that precedes cleaning of the target surface or object. Each cleaning operation may be performed by the individual wearing wearable computing device 12 with or without the aid of a tool (e.g., mop, brush, sprayer, sponge, wipe). Each cleaning operation may involve movement of the individual's hand, arm, and/or body in one or more dimensions. For example, a cleaning operation may involve a horizontal, vertical, and/or rotational movement of the hand corresponding to cleaning whereby force is transferred from the individual's hand to the target surface being cleaned, e.g., via a cleaning tool. For example, one type of cleaning operation that may be performed is a wiping cleaning movement in which the individual moves their body to wipe a target surface. Another type of cleaning operation that may be performed is a floor cleaning operation in which the individual performs a floor sweeping or mopping motion, e.g., in which the individual is standing upright and conveys force through a tool extending down to the floor surface. Another example of a type of cleaning operation that may be performed is an equipment cleaning operation. An equipment cleaning operation may be one in which the individual cleans equipment that is active or used during normal operation in the environment.

The surfaces or objects targeted for cleaning may be selected according to a cleaning protocol specifying surfaces that should be cleaned during a cleaning event. The specific surfaces selected for cleaning according to the protocol will vary depending on the application and environment in which the cleaning protocol is executed. Example surfaces that may be targeted for cleaning (e.g., in a hotel or healthcare environment) include, but are not limited to, those that define a light switch, a table top, a bed rail, a door knob, a medication dispensing pole, a television remote control, and combinations thereof. Other example surfaces that may be targeted for cleaning (e.g., in a food preparation environment) include, but are not limited to, those that define equipment used in the environment, such as a grill, a fryer, a refrigerator, a microwave, and combinations thereof.

In general, the types of surfaces targeted for cleaning may include floor surfaces and non-floor surfaces, which may be surfaces and objects elevated above the floor in which they reside. For example, the individual wearing wearable computing device 12 may perform a mopping, a sweeping, and/or deck brushing cleaning action on a floor surface. Additionally or alternatively, the individual wearing wearable computing device 12 may perform non-floor surface cleaning actions, such as cleaning a sink, faucet handle, toilet, countertop, etc. and combinations thereof. Each target surface may define an objection having flat horizontal surfaces, flat vertical surfaces, cavities, cylinders, spheres, and combinations thereof.

The individual performing a cleaning operation on each target surface while wearing wearable computing device 12 may perform the cleaning operation according to a protocol. The protocol may specify how the cleaning operation is to be performed on each target surface, e.g., a type of cleaning tool to be used, an extent of the surface to be cleaned, and/or a type and direction of force to be applied at one or more stages of the cleaning operation. In other words, the cleaning protocol may dictate a technique to be followed for cleaning each target surface, which will be followed while wearing wearable computing device 12 according to the training technique of FIG. 4 and is also instructed to be followed during subsequent cleaning events.

According to the technique of FIG. 4, sensor device 42 of wearable computing device 12 can generate movement data associated with movement of wearable computing device 12 during the cleaning operation performed on each of the plurality of target surfaces (102). Such movement data may be indicative of three-dimensional acceleration of wearable computing device 12 during the cleaning operation performed on each target surface and/or indicative of three-dimensional orientation of the wearable computing device during the cleaning operation. Other sensor data that may be generated include those data discussed above, such as GPS data.

Movement data generated by sensor device 42 of wearable computing device 12 during one or more training sessions can be associated with the cleaning of different target surfaces according to the technique of FIG. 4 (104). For example, one or more modules (e.g., module 26) executing within computing system 10 may receive the data generated by sensor device 42 and associate different portions of the movement data with a particular one of each of the plurality of target surfaces on which the individual wearing wearable computing device 12 has performed a cleaning operation.

For example, movement data generated by sensor device 42 of wearable computing device 12 may be wirelessly transmitted via network 16 to remote computing system 14 for analysis by one or more modules executing at the remote computing system. Different portions of the movement data generated by sensor device 42 may be associated with a corresponding target surface in a number of different ways. As one example, an individual associated with the training event may inform remote computing system 14 (e.g., via user interface 40) when a cleaning operation is being performed on a target surface (e.g., by indicating a start and a stop of the cleaning operation). In other words, an individual associated with the training event may assign cleaning of each target surface to a corresponding portion of movement data, allowing remote computing system 14 to associate movement data generated during a cleaning operation performed on a particular target surface to that target surface.

As another example, a communication unit associated with a tool used to clean a target surface and/or the target surface itself may provide an indication when that target surface is being cleaned. For example, wearable computing device 12 may receive communication signals from a tool associated with cleaning a particular target surface and/or a communication unit associate with the target surface target surface itself (e.g., near-field-communication radio, Wi-Fi radio, CB radio, Bluetooth radio, etc.), thereby indicating when that target surface is being cleaned. Remote computing system 14 can receive data corresponding to a time when the particular target surface is being cleaned (e.g., corresponding to the signal provided by the cleaning tool associate with the target surface and/or target surface emitter) and associate movement data corresponding with the cleaning operation on the target surface with that target surface.

Independent of the specific technique used to associate different portions of movement data generated during cleaning, the example technique of FIG. 4 includes determining reference data indicative of a cleaning operation being performed on a target surface for each of the plurality of different target surfaces (106). For example, a module executing on remote computing system 14 (e.g., a feature generation module) can process the movement data associated with each target surface to generate one or more features from the movement data indicative of a cleaning operation performed on that target surface. The movement data associated with a cleaning operation performed on each target surface can be filtered using a time-domain feature window and/or a frequency-domain window having a set duration (e.g., 1 second), with shorter duration windows providing more granularity. By contrast, longer duration windows provide reduced processing requirements and afford the opportunity for more cycles of cleaning motions (e.g., wiping, scrubbings, mop strokes) to manifest in the frequency domain. Candidate features for characterizing the movement data can be stored in a data store associated with remote computing system 14 and applied to the generate movement data. Each candidate feature may correspond to different aspects of a kinetic motion that makes up a cleaning operation associated with a particular target surface.

Candidate features can be generated for different aspects of the movement sensor data generated by sensor device 42 and/or different domains of the data. For example, when sensor device 42 is configured to generate inertial movement data (e.g., acceleration data, gyroscope data) across one or more axes, uniaxial and/or multiaxial features may be generated for the sensor data. Single axial features are transformation of a single inertial measurement unit (IMU) axis (e.g., acceleration or gyroscope reading in the x, y, or z axis). Sensitivity features can also be multiaxial features, which are transformations of multiple IMU axes at a given time point.

Additionally or alternatively, candidate features can be generated for different domains of the movement sensor data generated by sensor device 42. For example, time-domain features can be generated by applying transformations to each time-domain window of the sensor data. As another example, frequency-domain Fourier features can be generated by applying transformations to spectra arising from a discrete Fourier transform of the sensor data in each frequency domain window. As a further example, wavelet features can be generated by applied transformations to the spectra arising from a discrete wavelet transform of the sensor data in each frequency domain window.

One example class of features that may be generated are uniaxial time-domain features. Base functions that can be applied to the each time-domain window for each single axis IMU data—for example acceleration sensor data (e.g., x, y, and/or z) and/or gyroscope sensor data (e.g., x, y, and/or z)—include, but are not limited to: mean, median, variance, standard deviation, maximum, minimum, window range, root mean square (RMS), univariate signal magnitude area (SMA), zero-crossings, mean absolute jerk, standard deviation of absolute jerk, univariate SMA jerk, and combinations thereof.

Another example class of features that may be generated are multiaxial time-domain features. Base functions that can be applied to the each time-domain window across multiple axes of sensor data include, but are not limited to: xy-correlation, yz-correlation, xz-correlation, sum of signal magnitude area, mean of signal vector magnitude, standard deviation of signal vector magnitude, maximum xy-difference, maximum yz-difference, maximum xz-difference, and combinations thereof.

A further example class of features that may be generated are uniaxial-frequency-domain Fourier features. Base functions that can be applied to the spectra arising from the domain Fourier transform of the time domain signal in each frequency-domain window include, but are not limited to: DC offset, peak frequencies (e.g., top 3), peak amplitudes (e.g., top 3), and spectral energy.

A further example class of features that may be generated are uniaxial wavelet features. Base functions that can be applied to the spectra arising from the discrete wavelet transformation of the time domain signal in each frequency-domain window include, but are not limited to: wavelet persistence (e.g., in low, low-mid, mid-high, and high bands) and spectral energy (e.g., in low, low-mid, high-mid, and high bands).

Any or all candidate features can be generated for each duration segment of data generated by sensor device 42 of wearable computing device 12 and being associated with cleaning of a particular target surface. The features so generated can form a feature vector for each duration or time window of motion analyzed, with the time series of all such vectors forming a feature matrix from which feature selection is performed.

After generating a plurality of candidate features for characterizing the movement data associated with a cleaning operation performed in each target surface, one or more specific candidate features can be selected to define the reference movement data used in subsequent analysis and characterization of movement data during a cleaning event. Specific features can be selected from the pool of candidate features (e.g., by a module executing on remote computing system 14) based on the separability of the features in space. That is, features that adequately or best distinguish the desired reference data, for example cleaning of one target surface compared to different target surface target surface, can be selected.

Candidate features can be generated and selected using any type of supervised learning algorithm. Example supervised learning algorithms that can be used include, but are not limited to, a Bayesian network, a neural network, a k-nearest neighbor, a random forest, a support vector machine, and/or combinations of supervised learning algorithms, referred to as ensemble classifiers.

In the technique of FIG. 4, reference data for each target surface on which a cleaning operation was performed for characterization can be stored (e.g., in a data store 64 on wearable computing device 12 and/or a data store 28 on remote computing system 14) (108). Reference movement data may be stored in the form of raw data. Additionally or alternatively, reference movement data may be stored in the form of a feature set identified through the feature selection process discussed above that discriminates movement associated with a cleaning operation being performed on one target surface from movement associated with a cleaning operation being performed on each other target surface. Thus, it should be appreciated that discussion of reference movement data does not mean that the raw reference movement data need be used in subsequent analyses but rather data derived from or based on the raw reference movement data may be used. In any case, reference data associated with a cleaning operation being performed in each of the plurality of target surfaces may be stored for use in connection with the evaluation and/or characterization of subsequent cleaning events.

Figure 5:
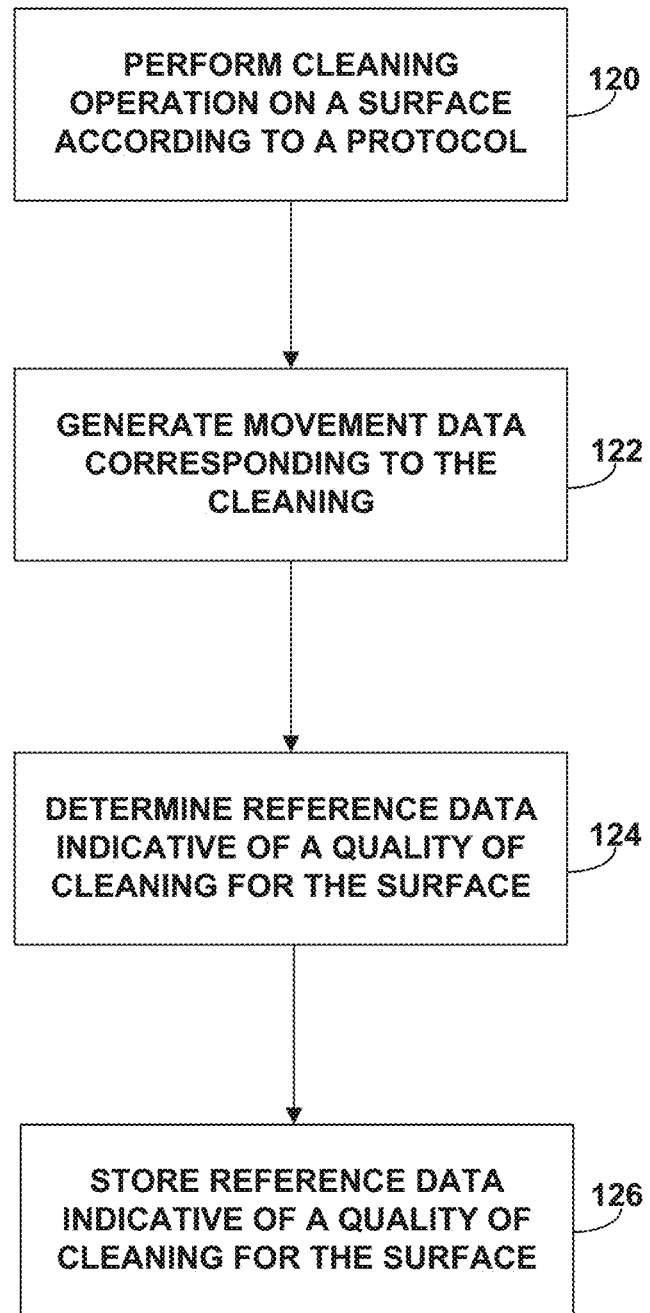
FIG. 5 is a flow diagram illustrating an example process for training an example wearable computing device to subsequently determine whether an individual performing cleaning has effectively cleaned the target surface to a threshold quality of cleaning.

FIG. 5 is a flow diagram illustrating an example process for training an example wearable computing device to subsequently determine whether an individual performing cleaning has effectively cleaned the target surface to a threshold quality of cleaning. The process shown in FIG. 5 may be performed by one or more processors of a computing device, such as wearable computing device 12 illustrated in FIGS. 1 and 2. For purposes of illustration, FIG. 5 is also described below within the context of computing system 10 of FIG. 1. It should be appreciated that the process of FIG. 5 may be performed by the individual who will be wearing wearable computing device 12 during subsequent cleaning or may be performed by a different individual (e.g., a trainer) other than the individual who will be performing the subsequently cleaning, as discussed above with respect to FIG. 4.

In the example of FIG. 5, an individual wearing wearable computing device 12 performs a cleaning operation on one or more target surfaces, the quality of cleaning of which is intended to be characterized during a subsequent cleaning event (120). The target surface may be any of those surfaces or objects discussed herein, including with respect to FIG. 4 above. Each target surface may define an object having boundaries in three-dimensional space that define an extent of the object to be cleaned.

The individual performing cleaning while wearing wearable computing device 12 may perform a cleaning operation on the target surface according to a protocol. The protocol may define a threshold quality of cleaning for the surface. For example, the protocol may be established such that compliance with the protocol indicates that the surface is clean to a threshold quality of cleaning whereas noncompliance with the protocol indicates that the surface is not cleaned to the threshold quality of cleaning.

The protocol may specify how the cleaning operation is to be performed on the target surface, e.g., a type of cleaning tool to be used, an extent of the surface to be cleaned, and/or a type and direction of force to be applied at one or more stages of the cleaning operation. For example, the cleaning protocol may dictate a technique to be followed for cleaning the target surface which, if followed while wearing wearable computing device 12 during a subsequent cleaning event, will indicate that the surface is clean to a threshold quality of cleaning. The protocol may be developed by cleaning specialist with knowledge of cleaning characteristics of different surfaces, pathogen killed times, and other experiential or laboratory data guiding development of a protocol to achieve a threshold quality of cleaning.

According to the technique of FIG. 5, sensor device 42 of wearable computing device 12 can generate movement data associated with movement of wearable computing device 12 during the cleaning operation performed on the target surface (122). In some examples, one or more modules executing within remote computing system 14 may receive the data generated by sensor device 42 for further processing. For example, movement data generated by sensor device 42 of wearable computing device 12 may be wirelessly transmitted via network 16 to remote computing system 14 for analysis by one or more modules executing at the remote computing system. Where the movement data generated by sensor device 42 includes movement data other than that associated with cleaning of the target object according to the protocol to establish the threshold quality of cleaning, a portion of the movement data generated by sensor device 42 corresponding to the cleaning can be associated with the cleaning, e.g., as discussed above with respect to FIG. 4.

The example technique of FIG. 5 includes determining reference data indicative of a threshold quality of cleaning performed on a target surface (124). For example, a module executing on remote computing system 14 (e.g., a feature generation module) can process the movement data associated with cleaning of the target surface to generate characteristics of the reference data. For example, raw movement data can be processed to generate a plurality of candidate features for characterizing the movement data associated with the quality of cleaning performed on the target surface, e.g., following the feature generation techniques discussed above with respect to FIG. 4. One or more specific candidate features can then be selected to define the reference movement data used in subsequent analysis and characterization of movement data generated during cleaning to characterize the quality of clean of the target surface, e.g., following the feature selection techniques discussed above with respect to FIG. 4.

Reference data generated for a target surface corresponding to a quality of cleaning of the target surface can be stored (e.g., in a data store 66 on wearable computing device 12 and/or a data store 30 on remote computing system 14) (126). Reference movement data may be stored in the form of raw data. Additionally or alternatively, reference movement data may be stored in the form of a feature set identified through the feature selection process that discriminates movement associated with a quality of cleaning performed on a target surface. Independent of the format of the data, reference data associated with a quality of clean performed on a surface may be stored for use in connection with the evaluation and/or characterization of a subsequent cleaning event.

Figure 6:
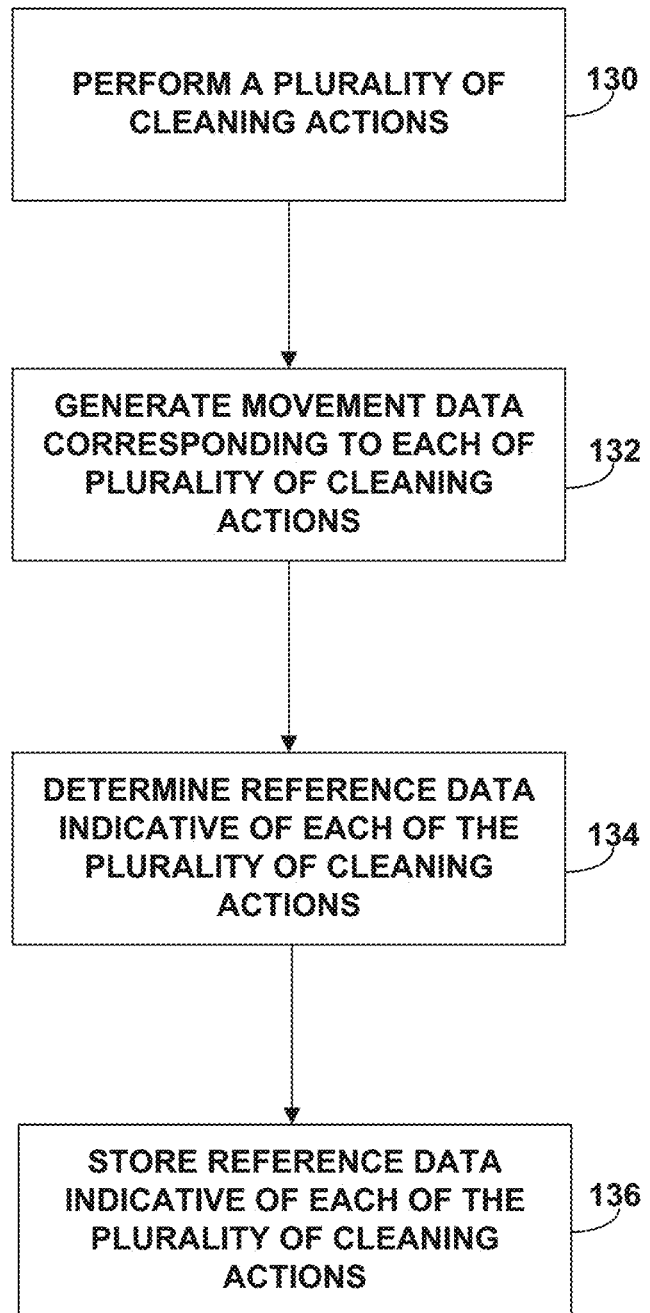
FIG. 6 is a flow diagram illustrating an example process for training an example wearable computing device to subsequently evaluate a plurality of different cleaning actions, e.g., as part of a total hygiene management system.

FIG. 6 is a flow diagram illustrating an example process for training an example wearable computing device to subsequently evaluate a plurality of different cleaning actions, e.g., as part of a total hygiene management system. The multiple different cleaning actions may include at least two different types of cleaning actions, such as three or more cleaning actions. Example cleaning actions that may be performed include floor surface cleaning actions, equipment cleaning actions, and hand hygiene cleaning actions. Other types of cleaning actions that may be performed include non-floor surface and non-equipment cleaning actions, such as cleaning actions performed on elevated surfaces (e.g., toilets, doorknobs, counters, and other surfaces such as those discussed above). The process shown in FIG. 6 may be performed by one or more processors of a computing device, such as wearable computing device 12 illustrated in FIGS. 1 and 2. For purposes of illustration, FIG. 6 is also described below within the context of computing system 10 of FIG. 1. It should be appreciated that the process of FIG. 6 may be performed by the individual who will be wearing wearable computing device 12 during subsequent cleaning or may be performed by a different individual (e.g., a trainer) other than the individual who will be performing the subsequently cleaning, as discussed above with respect to FIG. 4.

In the example of FIG. 6, an individual wearing wearable computing device 12 performs multiple different cleaning actions, each of which may be performed during a subsequent cleaning event (130). The target cleaning actions may include a non-hand hygiene cleaning action performed on any surface or object discussed herein, including with respect to FIG. 4 above. Each target surface may define an object having boundaries in three-dimensional space that define an extent of the object to be cleaned. The target cleaning actions may also include a hand hygiene cleaning action in which the wearer of the wearable computing device 12 cleans their hands.

The individual performing cleaning while wearing wearable computing device 12 may perform each cleaning action according to a corresponding protocol. For the non-hand hygiene cleaning actions, the protocol may specify how a cleaning operation is to be performed on a target surface, e.g., as discussed above with respect to FIGS. 3A-3C, 4, and 5. For the hand hygiene cleaning action, a corresponding hand hygiene clean protocol may be used. FIG. 7 illustrates an example hand hygiene protocol that may be specified for wearer of wearable computing device 12 to follow, although other protocols can be used.

According to the technique of FIG. 6, sensor device 42 of wearable computing device 12 can generate movement data associated with movement of wearable computing device 12 during each cleaning action performed and, optionally, between cleaning actions when non-cleaning actions are being performed (132). In some examples, one or more modules executing within remote computing system 14 may receive the data generated by sensor device 42 for further processing. For example, movement data generated by sensor device 42 of wearable computing device 12 may be wirelessly transmitted via network 16 to remote computing system 14 for analysis by one or more modules executing at the remote computing system. Where the movement data generated by sensor device 42 includes movement data multiple cleaning actions, a portion of the movement data generated by sensor device 42 corresponding to each cleaning action can be associated with that cleaning action, e.g., as discussed above with respect to FIG. 4.

The example technique of FIG. 6 includes determining reference data indicative of each type of cleaning action performed in which distinguishes each specific type of cleaning action from each other type of cleaning action (134). For example, a module executing on remote computing system 14 (e.g., a feature generation module) can process the movement data associated with each cleaning action to generate characteristics of the reference data. For example, raw movement data can be processed to generate a plurality of candidate features for characterizing the movement data associated with each cleaning action, e.g., following the feature generation techniques discussed above with respect to FIG. 4. One or more specific candidate features can then be selected to define the reference movement data used in subsequent analysis and characterization of movement data generated during the performance of multiple cleaning actions, e.g., following the feature selection techniques discussed above with respect to FIG. 4.

Reference data generated for each type of cleaning action can be stored (e.g., in a data store 68 on wearable computing device 12 and/or a data store 32 on remote computing system 14) (136). Reference movement data may be stored in the form of raw data. Additionally or alternatively, reference movement data may be stored in the form of a feature set identified through the feature selection process that discriminates movement associated with one specific type of cleaning action from each other specific type of cleaning action. Independent of the format of the data, reference data associated with each specific type of cleaning action may be stored for use in connection with the evaluation and/or characterization of a subsequent cleaning event.

The example calibration techniques described above with respect to FIGS. 4-6 may be performed on generic surfaces of similar character but having different dimensions than those surfaces actually cleaned in subsequent use. For example, one or more training sessions may be performed during which a representative substitute for the target surface to be cleaned is cleaned. As one example, a cleaning operation may be performed on a generic sink different than the actual sink to be cleaned during subsequent use. Data generated by cleaning the generic sink may be stored as reference movement data associated with cleaning of a sink and used to subsequently characterize the clean of the actual sink. The use of generic substitutes for the actual surfaces intended to be cleaned during subsequent use can facilitate the development of global, or non-customer-specific reference movement data sets.

In other implementations, the example calibration techniques described above with respect to FIGS. 4-6 may be performed on the actual surface (or a substantially exact replica thereof) to be cleaned in subsequent use. For example, one or more of the described calibration techniques may be performed in the environment in which cleaning efficacy is intended to be subsequently evaluated and on the actual target surface (or a substantially exact replica thereof) to generate more accurate reference movement data.

In subsequent use, cleaning efficacy determination module 26 can analyze movement data generated during a cleaning event with reference to comparative data stored in one or more data stores. Cleaning efficacy determination module 26 may determine if movement during the cleaning event is associated with cleaning action or non-cleaning action and/or determine whether movement during the cleaning event indicates that a cleaning action is in compliance with one or more standards.

In practice, certain cleaning events may deviate from a typical or planned course of cleaning. For example, a cleaning event may deviate from a planned course of cleaning where an area to be cleaned is significantly more soiled than is typically expected. This may necessitate extra cleaning on one or more surfaces beyond what a cleaning protocol for the surface(s) would otherwise specify. A heavily soiled area may also necessitate cleaning one or more surfaces that are not otherwise specified to be cleaned as part of a cleaning protocol. As another example, a cleaning event may be interrupted such that the individual performing cleaning does not complete a cleaning protocol. This may occur, for example, if the individual performing cleaning is reassigned to perform an alternative task during a cleaning event or if external conditions require termination of the cleaning event (e.g., an urgent patient need is identified by a cleaner performing maintenance cleaning of a patient's room in a healthcare environment).

User interface 40 of wearable computing device 12 may be configured to allow an individual associated with the wearable computing device to indicate when a cleaning event deviates from an expected cleaning protocol, e.g., because the cleaning protocol was not completed. User interface 40 may have include a physically-depressible button and/or may receive one or more gestures from a user of wearable computing device 12 (e.g., the user touching or pointing to one or more locations of the user interface) to indicate that the cleaning event is deviating from an excepted course of action such that a planned cleaning protocol is not executed as specified by the protocol.

A variety of different actions may be performed in response to a user input indicating that cleaning is deviating from a planned cleaning protocol. As one example, movement data associated with the cleaning event may be designated as deviating from the expected cleaning protocol. Movement data so designated may be filtered or otherwise separately treated from other movement data during one or move cleaning events not designated via user interface 40 as deviating from an expected protocol. This may allow more accurate cleaning validation information to be generated, displayed, and/or stored by separating abnormal cleaning events from standard cleaning events. Additionally or alternatively, the number and frequency of cleaning events designated as deviating from an expected protocol may be tracked and compared, e.g., to a threshold value and/or between different cleaners. This may provide insights into which cleaner(s) are experiencing more cleaning events designated as deviating from an expected protocol than other cleaners, potentially indicating supplemental training for the cleaner, changes to a particular cleaning protocol, and/or environmental changes to reduce the number of cleaning events designated as exceptional.

Figure 8:
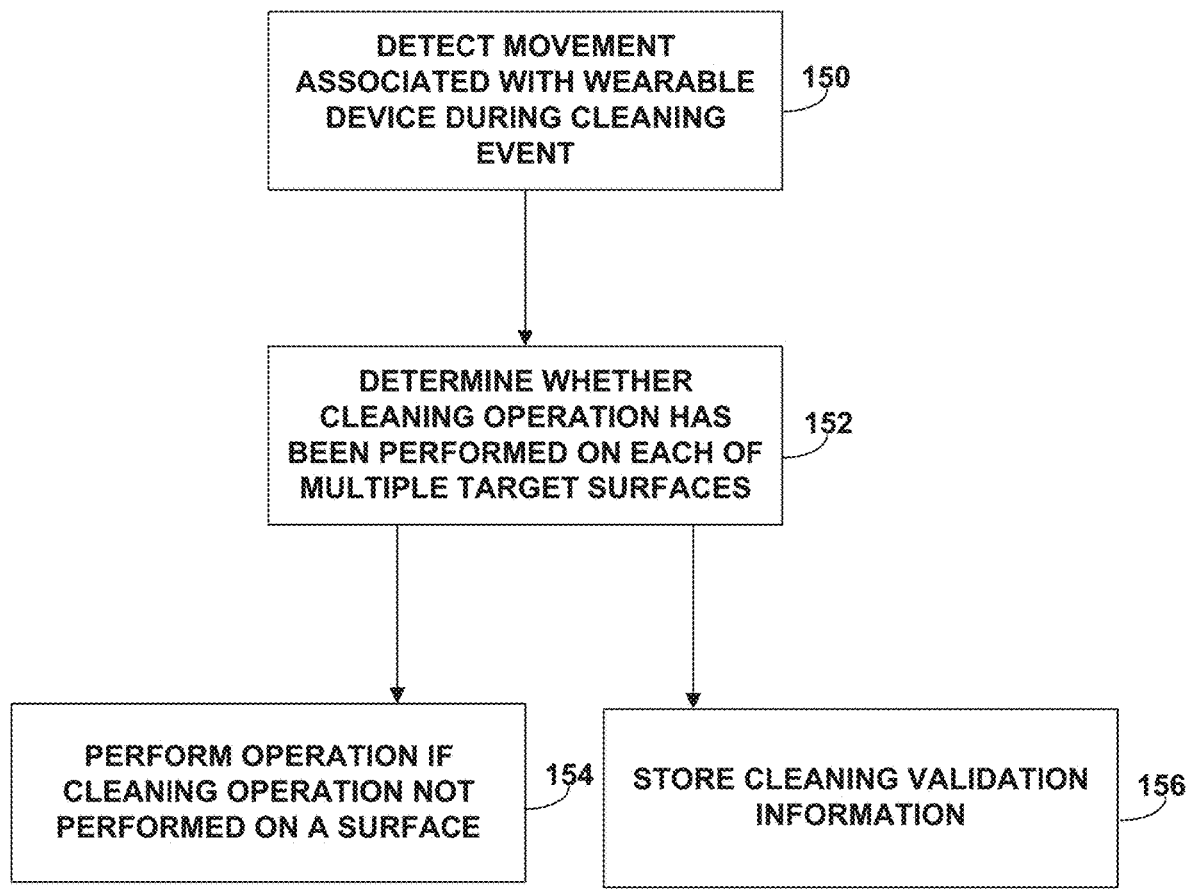
FIG. 8 is a flowchart illustrating an example operation of an example wearable computing device configured to track cleaning efficacy for reducing illnesses and infections caused by ineffective cleaning in accordance with one or more aspects of the present disclosure.

FIG. 8 is a flowchart illustrating an example operation of an example wearable computing device configured to track cleaning efficacy for reducing illnesses and infections caused by ineffective cleaning in accordance with one or more aspects of the present disclosure. The technique shown in FIG. 8 may be performed by one or more processors of a computing device, such as wearable computing device 12 and/or remote computing system 14.

In the example technique of FIG. 8, wearable computing device 12 can detect movement associated with the device during a cleaning event (150). The movement may be generated by an individual performing cleaning during the cleaning event, with multiple target surfaces intended to be cleaned during the event. Wearable computing device 12 may detect movement via sensor device 42 and generate movement data corresponding to the movement.

The plurality of surfaces targeted for cleaning during the cleaning event may be any surfaces and objects discussed herein, including those discussed with respect to FIG. 4. The individual performing cleaning during the cleaning event may be instructed to clean each of the plurality of target surfaces following a cleaning protocol, e.g., which may be the same protocol used to generate reference movement data corresponding to a cleaning operation being performed on each target surface.

At least one sensor of wearable computing device 12 may generate movement data corresponding to movement during a cleaning operation. One or more processors of wearable computing device 12 may receive the generated movement data and control transmission of the movement data, or data derived therefrom, to remote computing system 14. One or more processors 50 executing on remote computing system 14 may receive the data and execute instructions that cause cleaning efficacy determination module 26 to evaluate an efficacy of the cleaning performed.

Cleaning efficacy determination module 26 executing on remote computing system 14 may determine whether the individual performing cleaning has performed a cleaning operation on each of the plurality of surfaces targeted for cleaning (152). Cleaning efficacy determination module 26 can compare movement data generated by sensor device 42 of wearable computing device 12 during the cleaning event with reference movement data associated with cleaning of each of the plurality of target surfaces in data store 28 to make such determination. For example, cleaning efficacy determination model 26 may compare movement data generated throughout the duration of the cleaning event with reference movement data associated with each of the plurality of target surfaces, e.g., to determine if movement data generated at any period of time during the cleaning event corresponded to each of the plurality of target surfaces. If movement data generated during the cleaning event is not determined to be associated with reference data associate with at least one target surface, cleaning efficacy determination module 26 may determine that a cleaning operation was not performed on the target surface(s) during the cleaning event.

In some implementations, cleaning efficacy determination module 26 determines at least one signal feature for the received movement data to compare the movement data generated during the cleaning event to the reference movement data. For example, cleaning efficacy determination module 26 may determine a plurality of signal features for the received movement data generated by sensor device 42 during the cleaning event. The one or more signal features generated for the received movement data may correspond to those features selected during a calibration process to distinguish a cleaning operation performed on one target surface from a cleaning operation performed on different target surface. For example, the one or more signal features may correspond to those discussed above with respect to FIG. 4. Cleaning efficacy determination module 26 may compare the one or more signal features determined for the movement data generated during the cleaning event with reference signal feature data generated during calibration and stored in data store 28 corresponding to cleaning of each of the plurality of target surfaces, e.g., as discussed above with respect to FIG. 4.

When wearable computing device 12 is implemented with multiple sensors (e.g., including an accelerometer and a gyroscope), each of the multiple sensors may generate corresponding movement data during the cleaning event. Cleaning efficacy determination module 26 executing on remote computing system 14 may determine one or more signal features based on movement data generated by and received from each of the plurality of sensors. For example, cleaning efficacy determination module 26 may receive first movement data corresponding to an acceleration of wearable computing device 12 and second movement data corresponding to an angular velocity of the wearable computing device (for a gyroscope). Cleaning efficacy determination module 26 may determine at least one signal feature based on the first movement data and at least one additional signal feature based on the second movement data to characterize the movement performed during the cleaning event.

Depending on the characteristics of the surfaces targeted for cleaning, the individual wearing wearable computing device 12 may perform multiple different types of cleaning operations. For example, one type of target surface may be a horizontal surface (e.g., a countertop) having a horizontal wiping movement as a cleaning operation. Another type of target surface may be a vertical surface (e.g., a medication support portal) having a vertical wiping movement as a cleaning operation. Yet another type of target surface may be a doorknob having an arcuate shape to be cleaned characterized by yet a different type of cleaning operation with a rotary wiping movement. Thus, depending on the types of surfaces being cleaned and/or the protocol specified for cleaning each type of surface, the individual wearing wearable computing device 12 may perform one or more cleaning operations during the cleaning event.

In some examples, the individual performing cleaning performs at least a first cleaning operation for a first one of the plurality of target surface and a second cleaning operation different than the first cleaning operation for a second one of the plurality of target surfaces. In some additional examples, the individual performing cleaning performs a different cleaning operation on each one of the plurality of different surfaces targeted for cleaning.

The technique of FIG. 8 includes wearable computing device 12 performing an operation if it is determined that the individual performing cleaning has not performed a cleaning operation on at least one of the plurality of target surfaces (154). For example, user interface module 44 of wearable computing device 12 may receive information from remote computing system 14 via network 16 indicating that at least one of the surfaces targeted for cleaning during the cleaning event has not, in fact, had a cleaning operation performed on the surface. User interface module 44 may control wearable computing device 12 in response to receiving such an indication to perform one or more operations.

For example, user interface module 44 may perform an operation by controlling user interface 40 issue at least one of an audible, a tactile, and a visual alert. The alert may be a general alert notifying the wearer of wearable computing device 12 alert condition or may provide more specific information to the wearer about the content of alert. For example, the user alert may indicate via audible and/or visual (e.g., textual) delivery that the individual performing cleaning has not performed a cleaning operation on at least one of the target surfaces. In some examples, the user alert outputs information identifying the specific surface on which the user has not performed the cleaning operation, e.g., by describing the name or other identifying information of the target surface. In other implementations, wearable computing device 12 may perform an operation by communicating with an external system, such as a scheduling system, training system, or other system which utilizes data indicative of cleaning and/or hygiene performance.

The operation performed by wearable computing device 12 may be performed at any desired time, e.g., after determining that a cleaning operation has not been performed on target surface. For example, the operation controlling wearable computing device 12 to indicate that a cleaning operation was not performed on a target surface may be performed after the cleaning event is complete, e.g., as part of a training exercise and/or cleaning quality control evaluation. In other examples, the operation may be performed to issue an alert via wearable computing device 12 in substantially real-time with the performance of the cleaning event. For example, the alert may be issued while the individual is still performing cleaning is still conducting the cleaning event and/or in sufficient close enough temporal proximity to the termination of the cleaning event for the individual to perform a corrective cleaning operation (e.g., performed a cleaning operation on the one or more missed surfaces targeted for cleaning).

To help facilitate cleaning compliance and/or provide substantially real-time cleaning efficacy feedback, the individual performing cleaning may be instructed to perform a cleaning operation on each of the target surfaces in a target order. In other words, the individual performing cleaning may have a dictated sequential order in which the surfaces are to be cleaned. Cleaning efficacy determination module 26 can determine an order in which each surface on which a cleaning operation was performed was cleaned. Cleaning efficacy determination module 26 can compare the surface cleaning order to a target order in which each surface is expected to be cleaned, e.g., and determine if there any deviations between the actual order of cleaning in the target order of cleaning (e.g., stored in a data store of remote computing system 14 and/or wearable computing device 12). For example, cleaning efficacy determination module 26 may perform the order analysis in substantially real-time with the cleaning event, e.g., as a cleaning operation is performed on each surface, and may determine in substantially real-time with a target surface has been missed. Such target surface may be missed in that the individual performing cleaning forgot to perform a cleaning operation on the surface or in that the individual performing cleaning has neglected to clean the surface in the target order and has not yet returned to clean the surface.

In response to determining that the individual performing cleaning has not performed a cleaning operation on each of the plurality of target surfaces in the target order, a user alert may be issued by wearable computing device 12. The user alert may be any of the foregoing described user alerts and may or may not contain information identifying the incorrect order of cleaning operations performed. Additionally or alternatively, the information may be stored in a data store associated with wearable computing device 12 and/or remote computing system 14 identifying the order of cleaning operations performed (e.g., order of surfaces cleaned), optionally with a timestamp corresponding to the cleaning and/or information identifying the target order of cleaning.

In the example technique of FIG. 8, cleaning validation information may be stored in a data store associated with wearable computing device 12 and/or remote computing system 14 in addition to or in lieu of performing an operation (156). For example, in instances where cleaning efficacy determination module 26 determines that the individual performing cleaning has cleaned each of the plurality of target surfaces, cleaning validation information associated with the plurality of target surfaces, a time of the cleaning event (e.g. a time stamp), and/or other metadata corresponding to the context of measurement (e.g., room identification, GPS location) may be stored in a data store. Movement data generated by sensor device 42 associated with the cleaning event may or may not also be stored as part of a clean validation information. In either case, the cleaning validation information may provide quantifiable evidence that the individual performing cleaning has, in fact, performed the cleaning according to the required protocol standards. While cleaning validation information associated with compliant cleaning behavior may be stored, it should be appreciated that information associated with non-compliant behavior (e.g., cleaning not performed on all target surfaces) may also be stored, e.g., for training, analysis, and improvement.

In some implementations, cleaning efficacy determination module 26 may also evaluate a quality of cleaning performed by the wearer of wearable computing device 12 on one or more of the target surfaces deemed have been cleaned (e.g., on which a cleaning operation was performed). In one example, cleaning efficacy determination module 26 may compare a duration of a cleaning operation performed on a target surface to a threshold duration stored in a data store corresponding to a quality of cleaning. The threshold duration may specify a minimum amount of time each target surface should be cleaned, which may vary depending on the size and shape of the object and tendency to become contaminated. If cleaning efficacy determination module 26 determines that the duration of the cleaning operation performed on the target surface was equal to or greater than the threshold duration, the module may determine that the quality of clean performed on the target surface satisfied the threshold quality of cleaning.

Additionally or alternatively, cleaning efficacy determination module 26 may analyze movement data associated with cleaning of a specific target surface to reference movement data associate with a quality of cleaning of that target surface in data store 30. Additional details on an example process by which cleaning efficacy determination module 26 may determine a quality of cleaning with reference to data store 30 is described with respect to FIG. 9 below.

Figure 9:
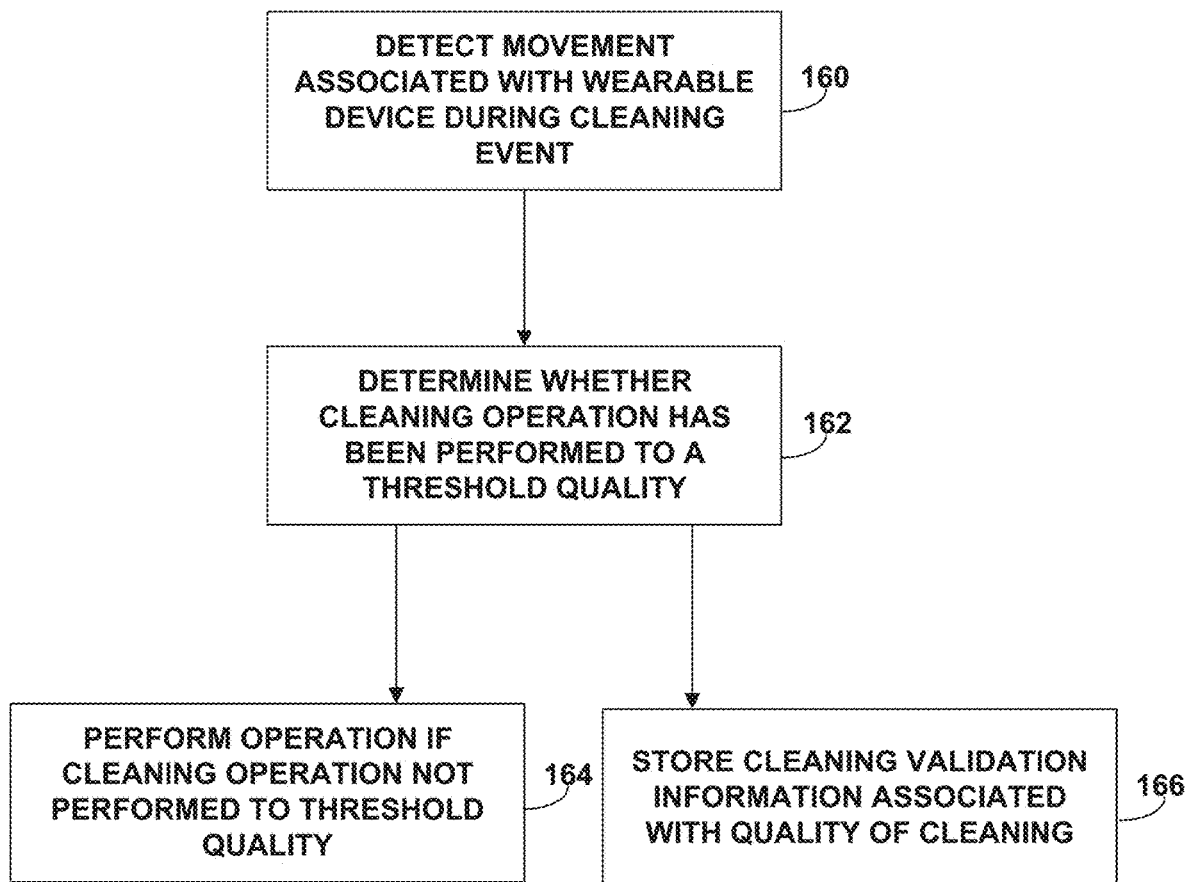
FIG. 9 is a flowchart illustrating another example operation of an example wearable computing device configured to track cleaning efficacy for reducing illnesses and infections caused by ineffective cleaning in accordance with one or more additional aspects of the present disclosure.

FIG. 9 is a flowchart illustrating example operation of an example wearable computing device configured to track cleaning efficacy for reducing illnesses and infections caused by ineffective cleaning in accordance with one or more additional aspects of the present disclosure. The technique shown in FIG. 9 may be performed by one or more processors of a computing device, such as wearable computing device 12 and/or remote computing system 14.

In the example technique of FIG. 9, wearable computing device 12 can detect movement associated with the device during a cleaning event (160). The movement may be generated by an individual performing cleaning during the cleaning event, with a target surface intended to be cleaned to a threshold quality of cleaning during the event. Wearable computing device 12 may detect movement via sensor device 42 and generate movement data corresponding to the movement.

The surfaces targeted for cleaning to a threshold quality of cleaning during the cleaning event may be any surface and object discussed herein, including those discussed with respect to FIG. 4. The individual performing cleaning during the cleaning event may be instructed to clean the surface following a cleaning protocol, e.g., which may be the same protocol used to generate reference movement data corresponding to a threshold quality of cleaning and stored in data store 30.

At least one sensor of wearable computing device 12 may generate movement data corresponding to movement during the cleaning operation. One or more processors of wearable computing device 12 may receive the generated movement data and control transmission of the movement data, or data derived therefrom, to remote computing system 14. One or more processors 50 executing on remote computing system 14 may receive the data and execute instructions that cause cleaning efficacy determination module 26 to evaluate and efficacy of the cleaning performed.

Cleaning efficacy determination module 26 executing on remote computing system 14 may determine whether the individual performing cleaning has cleaned the target surface with a threshold quality of cleaning (162). Cleaning efficacy determination module 26 can compare movement data generated by sensor device 42 of wearable computing device 12 during the cleaning event with reference movement data associated with a threshold quality of cleaning for the surface stored in data store 30 to make such determination.

In some implementations, cleaning efficacy determination module 26 determines at least one signal feature for the received movement data to compare the movement data generated during the cleaning event to the reference movement data. For example, cleaning efficacy determination module 26 may determine a plurality of signal features for the received movement data generated by sensor device 42 during the cleaning event. The one or more signal features generated for the received movement data may correspond to those features selected during a calibration process to establish a quality of cleaning for the surface. For example, the one or more signal features may correspond to those discussed above with respect to FIGS. 4 and 5. Cleaning efficacy determination module 26 may compare the one or more signal features determined for the movement data generated during the cleaning event with reference signal feature data generated during calibration and stored in data store 30 corresponding to a quality of cleaning for the surface, e.g., as discussed above with respect to FIG. 5.

When wearable computing device 12 is implemented with multiple sensors (e.g., including an accelerometer and a gyroscope), each of the multiple sensors may generate corresponding movement data during the cleaning event. Cleaning efficacy determination module 26 executing on remote computing system 14 may determine one or more signal features based on movement data generated by and received from each of the plurality of sensors. For example, cleaning efficacy determination module 26 may receive first movement data corresponding to an acceleration of wearable computing device 12 and second movement data corresponding to an angular velocity of the wearable computing device (for a gyroscope). Cleaning efficacy determination module 26 may determine at least one signal feature based on the first movement data and at least one additional signal feature based on the second movement data to characterize the movement performed during the cleaning event.

In some examples, cleaning efficacy determination module 26 receives movement data generated throughout the duration of the cleaning event that includes movement other than that associated with a cleaning operation being performed on the target surface. For example, the movement data may include periods of cleaning action and non-cleaning action. As another example, the movement data may include periods in which surfaces other than the target surface whose cleaning quality is being evaluated are cleaned.

Cleaning efficacy determination module 26 may segregate the movement data received from sensor device 42 by associating different portions of the movement data to different cleaning actions. For example, cleaning efficacy determination module 26 may associate a portion of the movement data received during the cleaning event with a time when the target surface is being cleaned. Cleaning efficacy determination module 26 may associate a portion of movement data with a particular surface being cleaned using any suitable technique, including those association techniques described above with respect to FIG. 4. Additionally or alternatively, cleaning efficacy determination module 26 may algorithmically break the movement data into periods corresponding to cleaning activity and non-cleaning activity, e.g., based on feature analysis of the movement data.

Accordingly, in some examples, cleaning efficacy determination module 26 may determine one or more signal features indicative of a quality of cleaning for only that portion of movement data corresponding to when the target surface is being cleaned, e.g., as opposed to the entire duration of the cleaning event. Cleaning efficacy determination module 26 can then compare the one or more signal features generated based on the associate movement data to reference movement data stored in data store 30.

In some examples, the reference movement data stored in data store 30 corresponds to a thoroughness of cleaning (e.g., indicative of the clean technique used and/or amount of work applied in performing the cleaning). Additionally or alternatively, the reference movement data stored in data store 30 may correspond to an area or extent of the target surface to be cleaned. For example, the reference movement data may define boundaries for the target surface in three-dimensional space. In these examples, cleaning efficacy determination module 26 can determine an area of cleaning performed on the target surface based on data generated by sensor device 42. The area of cleaning may correspond to a two or three-dimensional space over which a cleaning operation was performed. Accordingly, cleaning efficacy determination module 26 may determine a quality of cleaning by comparing an area of cleaning performed on the target surface to reference area data on the target surface stored in data store 30. Cleaning efficacy determination module 26 may determine if the area of cleaning performed on the target surface is greater than a threshold target area to be cleaned, e.g., to determine whether the cleaning operation satisfies the threshold quality of cleaning.

The technique of FIG. 9 includes wearable computing device 12 performing an operation if it is determined that the individual performing cleaning has not performed a threshold quality of cleaning on the surface (156). For example, user interface module 44 of wearable computing device 12 may receive information from remote computing system 14 via network 16 indicating that the surface targeted for cleaning during the cleaning event has not been cleaned to the threshold quality of cleaning. User interface module 44 may control wearable computing device 12 in response to receiving such an indication to perform one or more operations.

For example, user interface module 44 may perform an operation by controlling user interface 40 issue at least one of an audible, a tactile, and a visual alert. The alert may be a general alert notifying the wearer of wearable computing device 12 alert condition or may provide more specific information to the wearer about the content of alert. For example, the user alert may indicate via audible and/or visual (e.g., textual) delivery that the individual performing cleaning has not performed a cleaning operation on a surface to a threshold quality of cleaning.

The operation performed by wearable computing device 12 may be performed at any desired time. For example, the operation controlling wearable computing device 12 to indicate that a threshold quality of cleaning was not performed on a surface may be performed after the cleaning event is complete, e.g., as part of a training exercise and/or cleaning quality control evaluation. In other examples, the operation may be performed to issue an alert via wearable computing device 12 in substantially real-time with the performance of the cleaning event. For example, the alert may be issued while the individual is still performing cleaning and/or in sufficiently close temporal proximity to the termination of the cleaning event for the individual to perform a corrective cleaning operation (e.g., further clean the surface).

In some implementations, cleaning validation information may be stored in a data store associated with wearable computing device 12 and/or remote computing system 14 in addition to or in lieu of performing an operation (166). For example, in instances where cleaning efficacy determination module 26 determines that the individual performing cleaning has cleaned the target surface to the threshold quality of cleaning, cleaning validation information associated with the surfaces, a time of the cleaning event (e.g. a time stamp), and/or other metadata corresponding to the context of measurement (e.g., identification of the surface, GPS location) may be stored in a data store. Movement data generated by sensor device 42 associated with the cleaning event may or may not also be stored as part of the cleaning validation information. In either case, the cleaning validation information may provide quantifiable evidence that the individual performing cleaning has, in fact, performed the cleaning according to the required quality standards. While cleaning validation information associated with compliant cleaning behavior may be stored, it should be appreciated that information associated with non-compliant behavior (e.g., cleaning not satisfying a threshold quality of cleaning) may also be stored, e.g., for training, analysis, and improvement.

Figure 10:
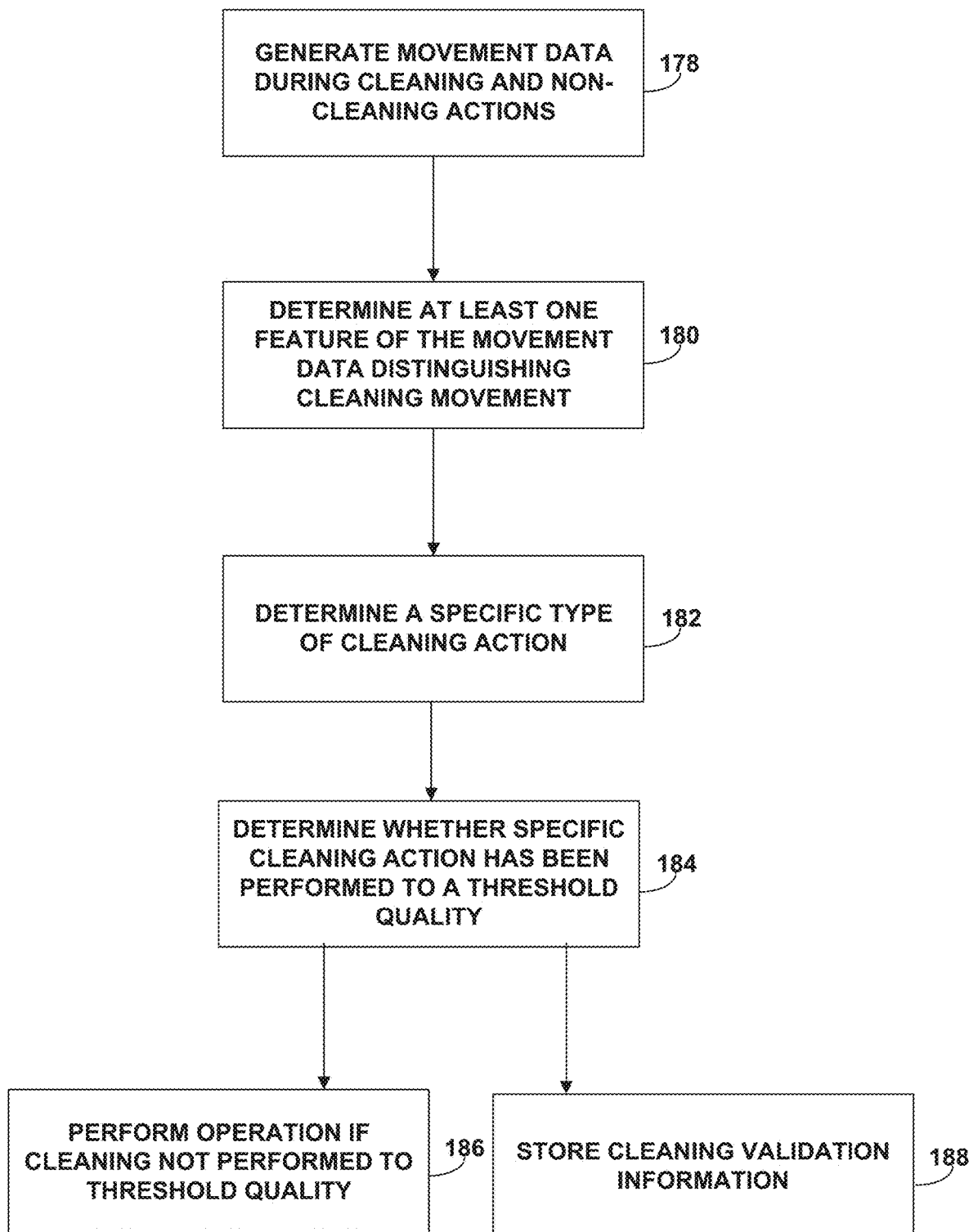
FIG. 10 is a flowchart illustrating example operation of an example wearable computing device configured to track cleaning efficacy for total hygiene management in accordance with one or more aspects of the present disclosure.

FIG. 10 is a flowchart illustrating example operation of an example wearable computing device configured to track cleaning efficacy for total hygiene management in accordance with one or more aspects of the present disclosure. The technique shown in FIG. 10 may be performed by one or more processors of a computing device, such as wearable computing device 12 and/or remote computing system 14.

In the example technique of FIG. 10, wearable computing device 12 can generate movement data during a course of activity that may include cleaning actions and non-cleaning actions (178). The movement data may be generated by an individual performing activity, e.g., during a cleaning event. The clean activity may correspond to one or more specific types of clean actions, whereas the non-cleaning actions may correspond to movement before, between, and/or after cleaning actions.

At least one sensor of wearable computing device 12 may generate movement data corresponding to movement by the wearer of the wearable computing device, e.g., during cleaning and non-cleaning actions. One or more processors of wearable computing device 12 may receive the generated movement data and control transmission of the movement data, or data derived therefrom, to remote computing system 14. One or more processors 50 executing on remote computing system 14 may receive the data and execute instructions that cause cleaning efficacy determination module 26 to evaluate an efficacy of the cleaning performed.

Cleaning efficacy determination model 26 executing on remote computing system 12 may determine at least one feature of the movement data indicating that the wearer of wearable computing device 12 is performing a cleaning action (180). The one or more signal features generated for the received movement data may correspond to those features selected during a calibration process to discriminate cleaning from non-cleaning actions. For example, the one or more signal features may correspond to those discussed above with respect to FIGS. 4 and 6. Cleaning efficacy determination module 26 may compare the one or more signal features determined for the movement data generated received from wearable computing device 12 with reference signal feature data generated during calibration and stored in data store 32.

When wearable computing device 12 is implemented with multiple sensors (e.g., including an accelerometer and a gyroscope), each of the multiple sensors may generate corresponding movement data during the cleaning event. Cleaning efficacy determination module 26 executing on remote computing system 14 may determine one or more signal features based on movement data generated by and received from each of the plurality of sensors. For example, cleaning efficacy determination module 26 may receive first movement data corresponding to an acceleration of wearable computing device 12 and second movement data corresponding to an angular velocity of the wearable computing device (for a gyroscope). Cleaning efficacy determination module 26 may determine at least one signal feature based on the first movement data and at least one additional signal feature based on the second movement data to characterize the movement performed during the cleaning event.

Example types of cleaning actions that may be performed include environmental cleaning actions in which one or more surfaces in environment 18 are cleaned. Examples of these types of cleaning actions include floor surface cleaning actions (e.g., sweeping, mopping) and non-floor surface cleaning actions (e.g., cleaning equipment within an environment 18). Another type of cleaning action that may be performed is a personal cleaning action, such as a hand hygiene cleaning event in which an individual conducts a handwashing protocol (e.g., with an alcohol-containing sanitizer, with soap and water). By contrast, non-cleaning actions may be any activity the generates movement data not associated with personal or environmental cleaning activity.

The example technique of FIG. 10 further includes determining a specific type of cleaning action performed from the movement data generated by wearable computing device 12 (182). For example, cleaning efficacy determination model 26 executing on remote computing system 12 may determine at least one feature of the movement data corresponding to each of the multiple types of clean actions performed and for which movement data was generated by wearable computing device 12. The one or more signal features generated for the received movement data may correspond to those features selected during a calibration process to discriminate each specific type of cleaning activity from each other specific type of cleaning activity. For example, the one or more signal features may correspond to those discussed above with respect to FIGS. 4 and 6. Cleaning efficacy determination module 26 may compare the one or more signal features determined for the movement data associated with each cleaning activity with reference signal feature data generated during calibration and stored in data store 32.

In the example of FIG. 10, cleaning efficacy determination module 26 may analyze movement data associated with one or more specific types of cleaning actions with reference to movement data associated with a quality of cleaning of that specific type of cleaning action in data store 30 (184). Additional details on an example process by which cleaning efficacy determination module 26 may determine a quality of cleaning for a specific type of cleaning action with reference to data store 30 is described with respect to FIG. 9 above.

In some implementations, the individual performing multiple cleaning actions may be instructed to perform each cleaning action in a target order. In other words, the individual performing cleaning may have a dictated sequential order in which different cleaning actions are to be performed. For example, the dictated order may specify that the individual perform all non-hand-hygiene cleaning actions and then perform a hand hygiene cleaning action (e.g., before then performing non-cleaning activities).

Cleaning efficacy determination module 26 can determine an order in which each specific type of cleaning action was performed. Cleaning efficacy determination module 26 can compare the cleaning action order to a target order in which each action is expected to be performed, e.g., and determine if there any deviations between the actual order of cleaning and the target order of cleaning (e.g., which may be stored in a data store of remote computing system 14 and/or wearable computing device 12). For example, cleaning efficacy determination module 26 may perform the order analysis in substantially real-time with the cleaning actions being performed.

In response to determining that the individual wearing wearable computing device 12 has not performed each cleaning action in the target order, a user alert may be issued by wearable computing device 12. The user alert may be any of the foregoing described user alerts and may or may not contain information identifying the incorrect order of cleaning actions performed. Additionally or alternatively, the information may be stored in a data store associated with wearable computing device 12 and/or remote computing system 14 identifying the order of cleaning actions performed, optionally with a timestamp corresponding to the cleaning and/or information identifying the target order of cleaning.

The technique of FIG. 10 includes wearable computing device 12 performing an operation if it is determined that the individual performing a specific type of cleaning action has not performed a threshold quality of cleaning for the action (186). For example, user interface module 44 of wearable computing device 12 may receive information from remote computing system 14 via network 16 indicating that the specific cleaning action (e.g., hand hygiene action or non-hand hygiene action) has not been performed to the threshold quality of cleaning. User interface module 44 may control wearable computing device 12 in response to receiving such an indication to perform one or more operations.

For example, user interface module 44 may perform an operation by controlling user interface 40 issue at least one of an audible, a tactile, and a visual alert. The alert may be a general alert notifying the wearer of wearable computing device 12 alert condition or may provide more specific information to the wearer about the content of alert. For example, the user alert may indicate via audible and/or visual (e.g., textual) delivery that the individual performing cleaning has not performed a cleaning action to a threshold quality of cleaning. In other examples, the operation may be performed to issue an alert via wearable computing device 12 in substantially real-time with the performance of the cleaning action. For example, the alert may be issued while the individual is still performing cleaning action and/or in sufficiently close temporal proximity to the termination of the cleaning action for the individual to perform a corrective cleaning action (e.g., further clean).

In some implementations, cleaning validation information may be stored in a data store associated with wearable computing device 12 and/or remote computing system 14 in addition to or in lieu of performing an operation (188). Movement data generated by sensor device 42 associated with cleaning action(s) may or may not also be stored as part of the cleaning validation information. In either case, the cleaning validation information may provide quantifiable evidence that the individual performing cleaning has, in fact, performed certain cleaning actions and/or performed the cleaning action(s) according to the required quality standards. While cleaning validation information associated with compliant cleaning behavior may be stored, it should be appreciated that information associated with non-compliant behavior (e.g., cleaning not satisfying a threshold quality of cleaning) may also be stored, e.g., for training, analysis, and improvement.

As initially discussed above with respect to FIG. 1, user interface module 44 may cause user interface 40 of wearable computing device 12 to present audio (e.g., sounds), graphics, or other types of output (e.g., haptic feedback, etc.) associated with a user interface. The output may be responsive to one or more cleaning determinations made and, in some examples, may provide cleaning information to the wearer of wearable computing device 12 to correct cleaning behavior determined to be noncompliant. For example, when cleaning efficacy determination module 26 determines whether or not the user has performed certain compliant cleaning behavior (e.g., performed a cleaning operation on each surface targeted for cleaning, cleaned a target surface to a threshold quality of cleaning, and/or performed a specific type of cleaning action and/or perform such action to a threshold quality of cleaning), user interface module 44 may control wearable computing device 12 to output an alert concerning the compliant or non-compliant action.

In addition to or in lieu of controlling user interface 40 based on compliance or non-compliance with certain cleaning behavior, user interface 40 of wearable computing device 12 may provide information to help guide a user through a cleaning protocol. For example, user interface 40 may provide audible, tactile, and/or visual information informing the user of wearable computing device 12 of the cleaning protocol to be performed. The information may provide step-by-step instructions, such as providing an order of surfaces to be cleaned and/or order of cleaning techniques to be performed on one or more surfaces being cleaned.

In some implementations, completion of a specific step of a cleaning protocol (e.g., cleaning a specific surface, using a specific cleaning technique on a surface) is automatically detected based on movement data generated by wearable computing device 12. User interface 40 may issue information informing the user of the next step of the cleaning protocol to be performed in response to automatically detecting completion of the preceding step of the protocol. Additionally or alternatively, a user may interact with user interface 40 to manually indicate that a specific step of a cleaning protocol has been completed and/or navigate to guidance output for a different step of the cleaning protocol. User interface 40 may issue information informing the user of the step of the cleaning protocol to be performed in response to the manual input of the user, such as information informing the user of the next step of the cleaning protocol to be performed in response to an indication that the preceding step of the protocol was completed.

FIGS. 17A-17D illustrate of an example sequential series of user interface graphics that may be displayed to a user to help guide execution of a cleaning protocol. FIG. 17A illustrates an example wearable computing device 12 with an image of a dresser or bedside table, guiding the user to clean the dresser or bedside table. FIG. 17B illustrates the example wearable computing device with an image of a tray table, guiding the user to clean the tray table after completing cleaning of the dresser or bedside table. FIG. 17C illustrates the example wearable computing device with an image of a chair, guiding the user to clean the chair after completing cleaning of the tray table. FIG. 17D illustrates the example wearable computing device with an image of a light switch, guiding the user to clean the light switch after completing cleaning of the chair.

In the examples described above, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements.

The techniques of this disclosure may be implemented in a wide variety of devices or apparatuses. Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

The following example may provide additional details on hygiene tracking and compliance systems and techniques according to the disclosure.

EXAMPLE

An experiment was performed to evaluate the ability to track and/or monitor cleaning activity using a wearable device. The experiment was replicated several times using different datalogger apps executing on a mobile phone as well as standalone devices (e.g., smart watch) that were affixed to various anatomical locations (wrist, arm, pocket). The results provided by each device configuration were consistent.

In this specific example, a wrist-worn inertial measurement unit (IMU) having a three-axis accelerometer and three-axis gyroscope was utilized to obtain measurement data. A single subject performed a cleaning sequence as follows: (1) 4 slow back-and-forth wipes of a table top followed by (2) 7 quick scrubs of the table top followed by (3) a single slow circular wipe of the table top. The subject paused for several second between each of the cleaning motions.

Figure 11:
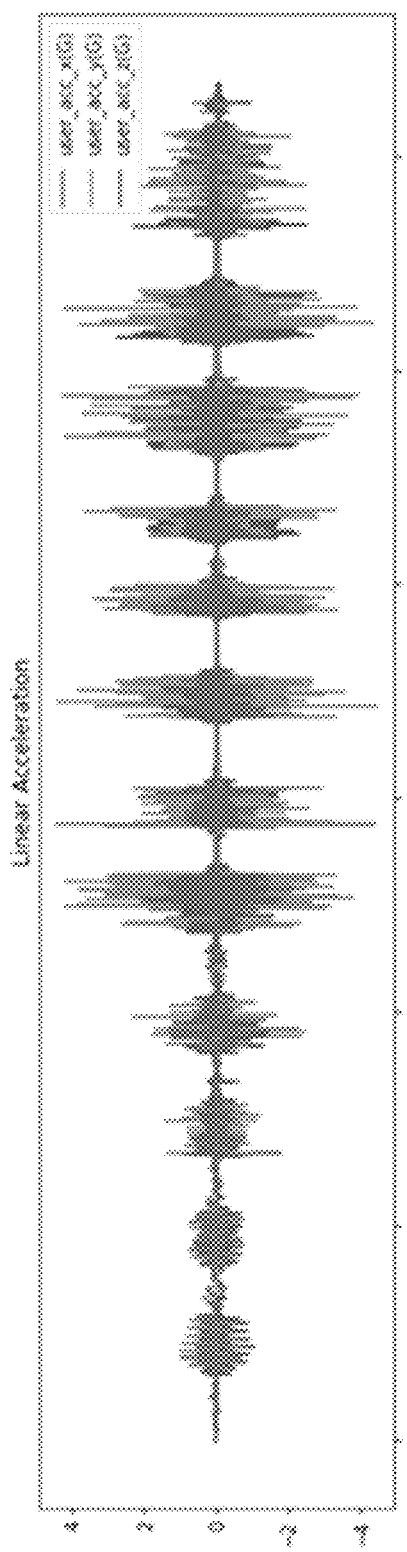
FIGS. 11 and 12 are plots of the linear acceleration and rotation rate data, respectively, generated during an experiment.
Figure 12:
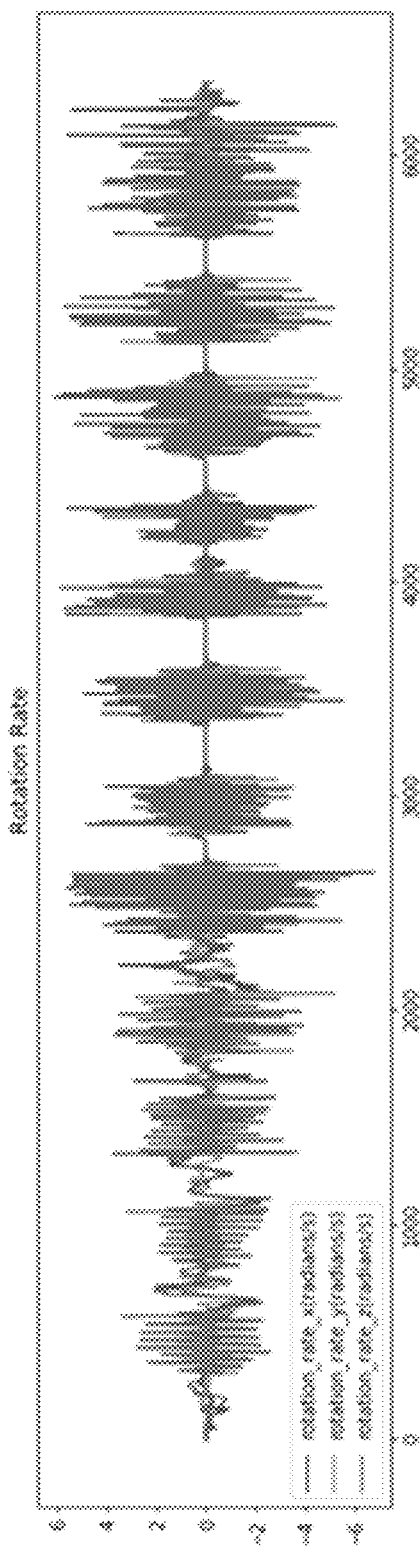

The wrist-worn IMU generated raw data sampled at 50 Hz and included of 6 quantities: (1) Linear acceleration in the x-, y-, and z-axes (sampled from a triaxial accelerometer) and (2) Rotation rate about the x-, y-, and z-axes (sampled from a triaxial gyroscope). The experimental session lasted 126 seconds and produced 126×50=6300 rows of these 6 values in time series. FIGS. 11 and 12 are plots of the linear acceleration and rotation rate data generated during the experiment.

The session was video-recorded and two sequences of activity labels were produced: (1) A binary target: cleaning or not cleaning, and (2) A multiclass target: wiping, scrubbing, or not cleaning. Supervised learning involves training a model from an initial training set of labelled data, and the given target sequence determines the type of predictive model the pipeline will train (binary or multiclass). For simplicity, only a technique variation (wiping vs scrubbing) is included in this experiment to create a multiclass target. In general, many other multiclass labels are possible, including: tool used, target of cleaning, technique of cleaning, or any combination thereof.

The wearable IMU data was filtered for further processing. The data was subject to various sources of noise that can impact the signal quality, including a loose-fit for the wearable, contact with a garment, and/or sudden collisions with ambient objects. As such, it was desirable to smooth the data via a filtering operation. The algorithm used provided an N-point moving median filter that effectively removed undesirable spikes and troughs in the raw data.

Figure 13:
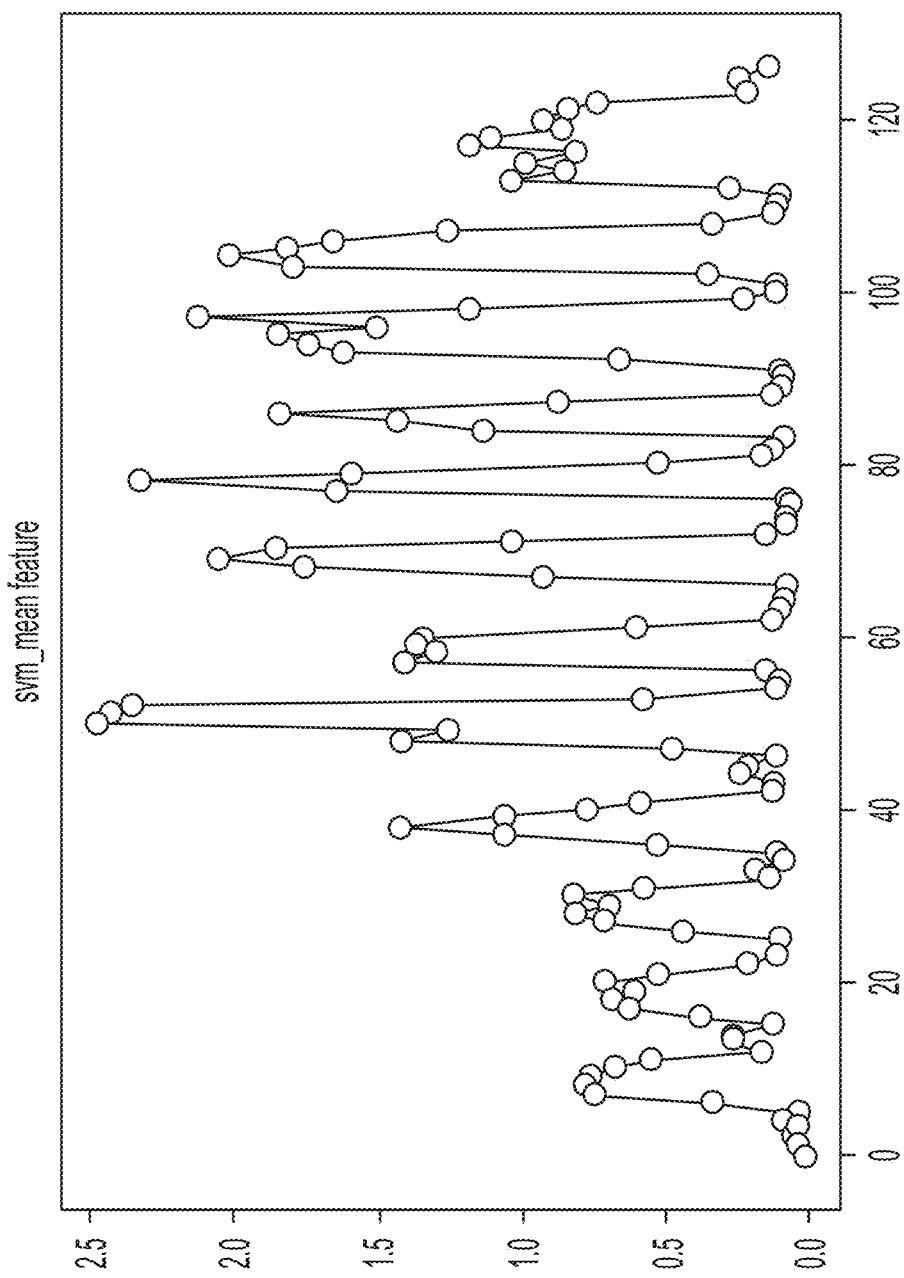
FIG. 13 illustrates an example single time-domain feature representation generated from raw sample data for the experiment of FIGS. 11 and 12.

After filtering, two sliding windows were passed over the data to generate a feature matrix: a is time-domain feature window and a 5 s frequency-domain window. The frequency-domain window completely overlapped the time-domain window so that as both windows slide every second, only is of new data were covered by the 5 s frequency domain window. The frequency-domain window also doubled as a window for the generation of wavelet features. FIG. 13 illustrates an example single time-domain feature representation generated from the raw sample data.

At the next step of the data analysis process, candidate features were generated for the data to expose different aspects of the primitive kinetic motions that make up cleaning activities. Each feature illustrates a compact second-by-second representation of the original raw data. The candidate generation step created features combinatorially by applying transformations to base functions (i.e., transforms) in different feature families, as discussed above with respect to FIG. 4. For the experimental data, a total of 189 candidate features were generated for every second of filtered data, forming a feature vector for that second of motion. The time series of all such vectors formed a feature matrix from which feature selection was performed.

During feature selection, a feature selection routine was specified to select the dimensions which best discriminate the activity targets in feature space. As implemented, the number of top features was a configurable parameter at feature selection time, but all 189 received a score and ranking. For the experimental data, top five features selected for binary target classification were as follows:

TABLE 1

Feature selection ranking for experimental data.

| Feature | Score |
| --- | --- |
| gz_std | 214 |
| gz_window_range | 194 |
| sma_sum | 191 |
| x_std | 189 |
| svm_mean | 189 |

Figure 14:
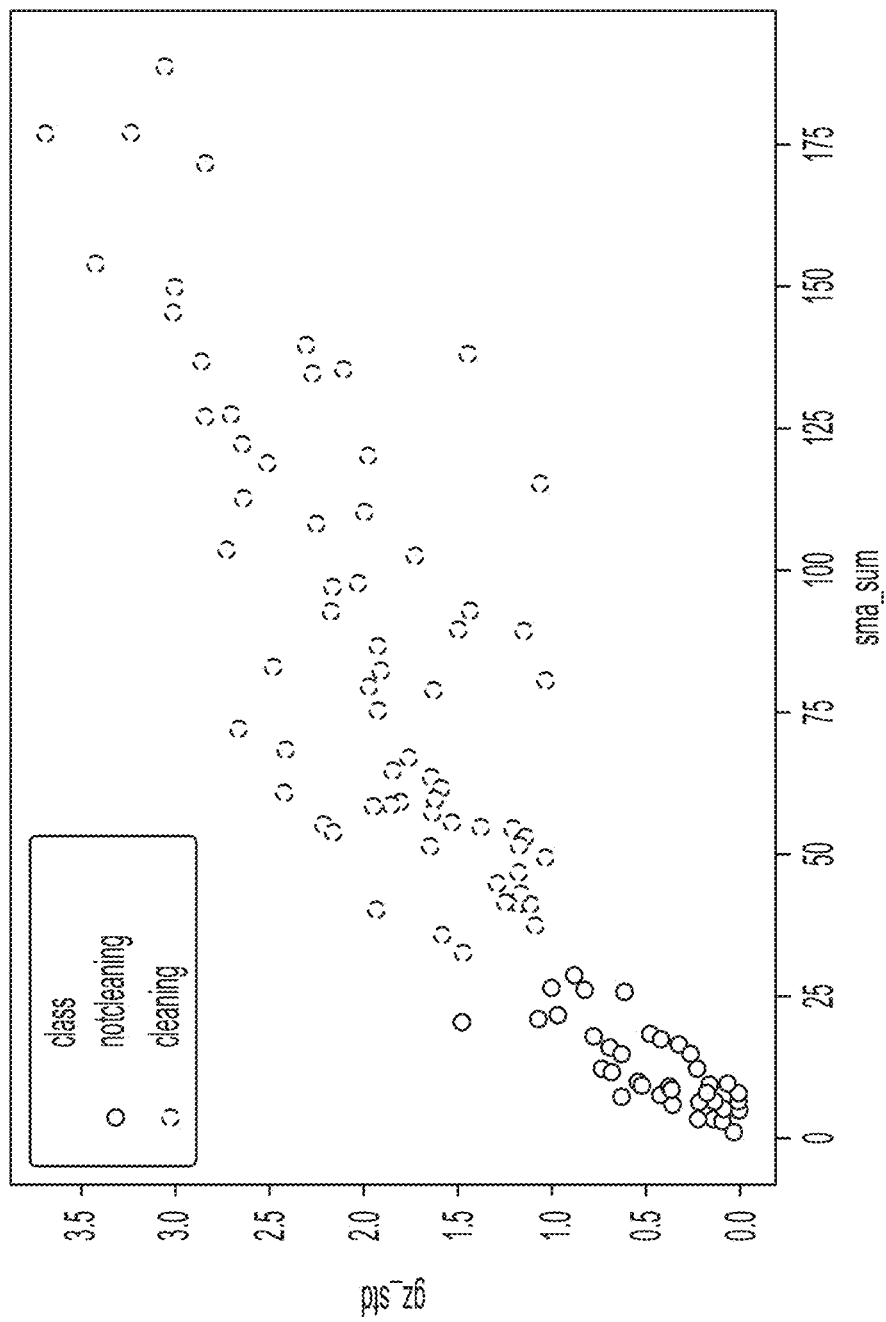
FIG. 14 illustrates the top two features determined from the candidate features for binary classification for the experimental data of FIGS. 11-13.

What makes a feature a good candidate is that it separates well the classes in feature space. Pairs and triples of feature spaces can be rendered via scatterplots with the activity classes labeled in different colors. FIG. 14 illustrates the top two features determined from the candidate features for binary classification of the experimental data. The data show these two features provide good linear separability between the target classes (cleaning, not cleaning). More features were needed for accurate classification into more classes (not cleaning, scrubbing, and wiping).

Following feature selection, a feature matrix is appended to the second-by-second target labels to make a training set for a supervised learning classifier. The exact classification algorithm was a parameter passed to the pipeline. Various classification algorithms were tested, but the class of ensemble classifiers that tended to perform effective (in both the binary and multiclass setting) for the experimental data was a random forest classifier. The following Tables are classification reports for a 10-feature random forest evaluated by 10-fold cross-validation applied to the experimental data:

TABLE 2

Binary Classification Results for sample session

| | precision | recall | f1-score | support |
| --- | --- | --- | --- | --- |
| cleaning | 0.90 | 0.98 | 0.94 | 66 |
| notcleaning | 0.98 | 0.89 | 0.93 | 61 |
| avg/total | 0.94 | 0.94 | 0.94 | 127 |

Total (s): 127, Predicted Positive (s): 72, Actual Positive (s): 66

TABLE 3

Multiclass Classification Results for sample session

| | precision | recall | f1-score | support |
| --- | --- | --- | --- | --- |
| notcleaning | 0.82 | 0.87 | 0.84 | 61 |
| scrubbing | 0.85 | 0.81 | 0.83 | 36 |
| wiping | 0.86 | 0.80 | 0.83 | 30 |
| avg/total | 0.84 | 0.83 | 0.83 | 127 |

Figure 15:
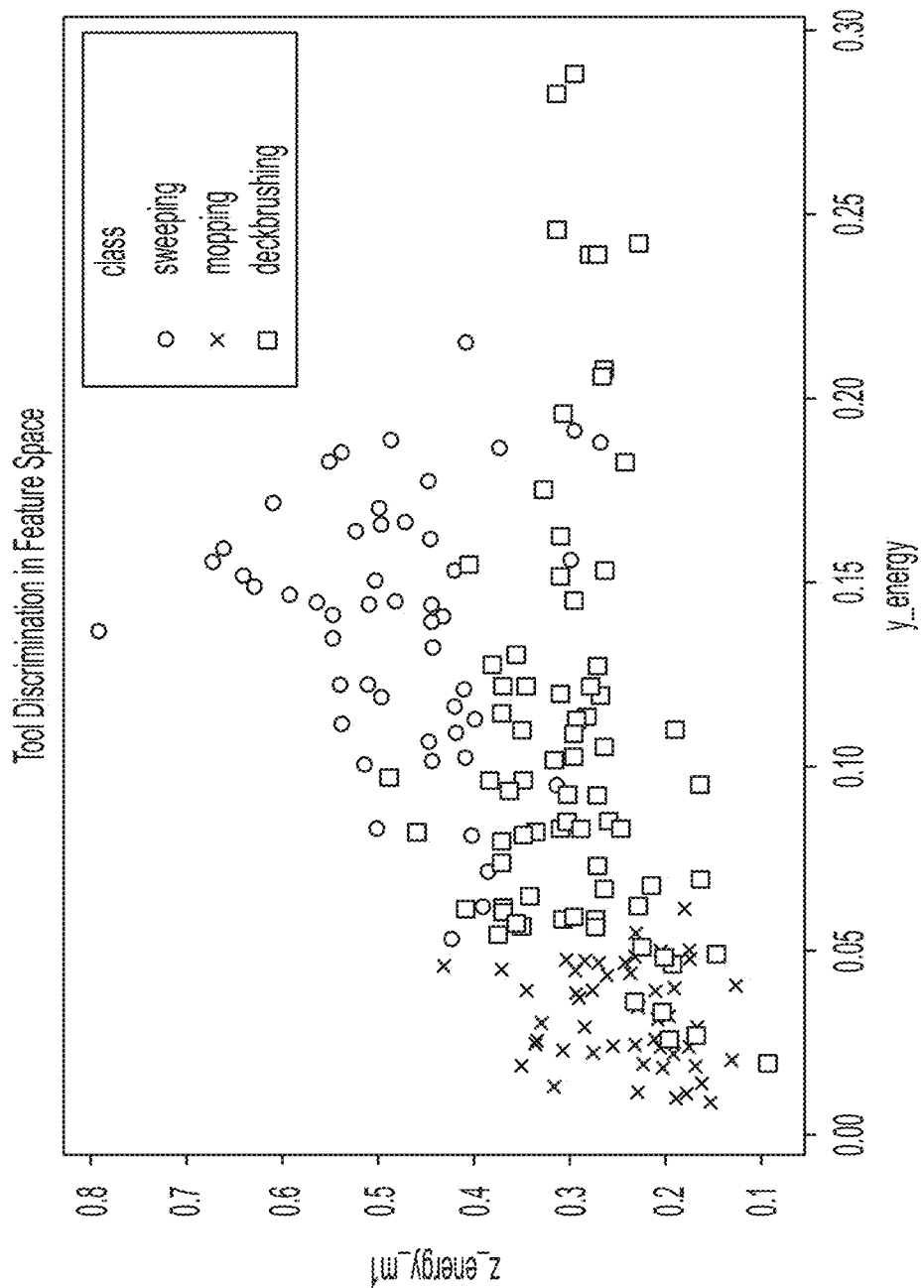
FIG. 15 is a plot showing discrimination of three example types of tools used as part of a mock restaurant context floorcare study utilizing movement data.
Figure 16:
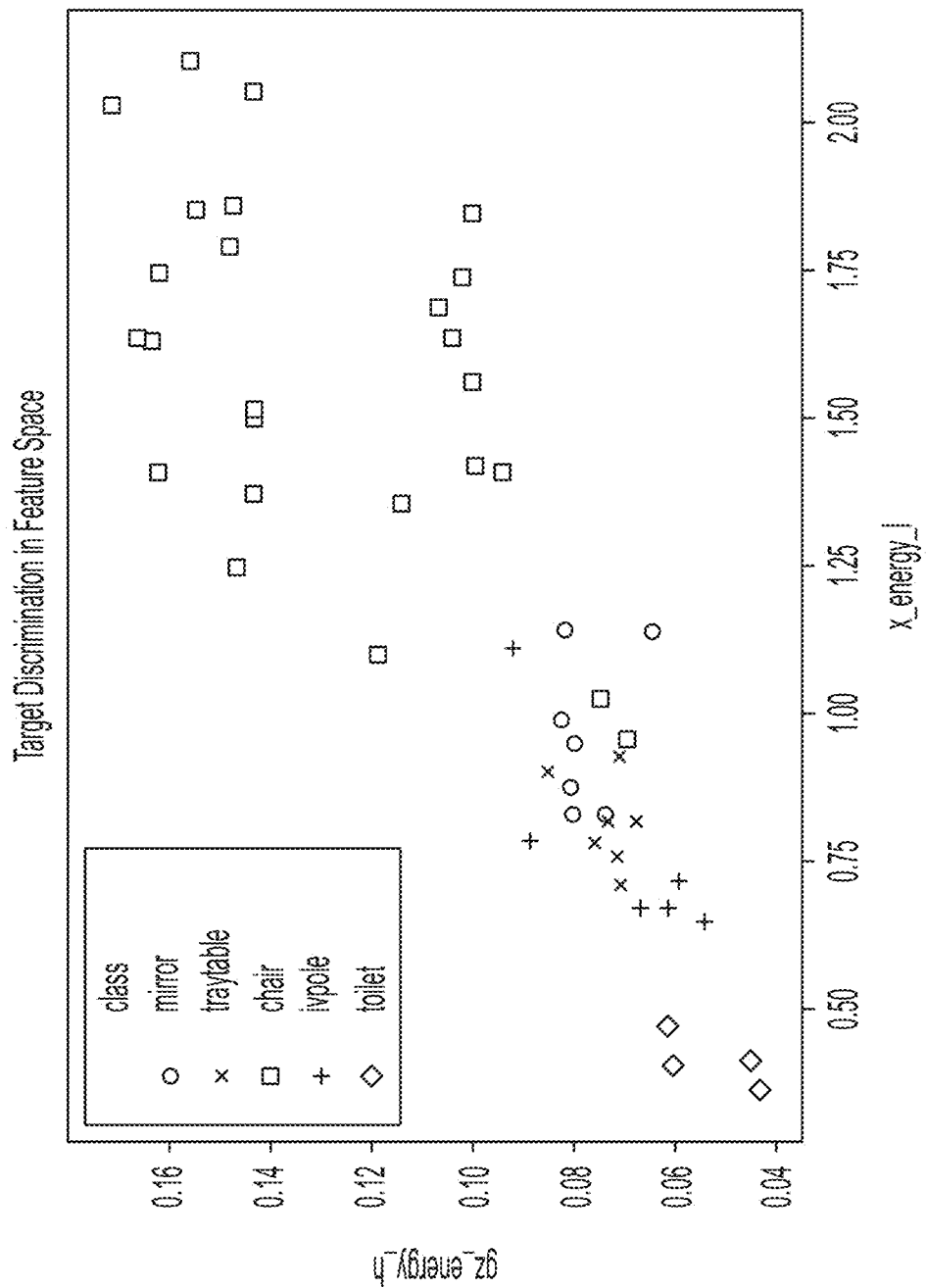
FIG. 16 is a plot showing discrimination of five example target surfaces performed as part of a mock hospital context study utilizing movement data.

In the preceding example, the multiclass labeling used to train a model segmented cleaning motions by technique alone (wiping vs scrubbing). More generally, a cleaning classifier output can utilize a combination of tools, targets, and techniques in labeling training samples. Each of these may carve out predicted cleaning acts in a more natural way: (1) Tool: The cleaning apparatus being handled by the subject in the cleaning act (e.g., rag, toilet brush, mop, broom, duster); (2) Target: The collection of surfaces that constitute the object the subject is cleaning; (3) Technique: The manner in which the cleaning act is executed by the subject. FIG. 15 is a plot showing discrimination of three types of tools performed as part of a mock restaurant context floorcare study utilizing movement data: a broom (sweeping), a mop, and a deck brush. FIG. 16 is a plot showing discrimination of five target surfaces performed as part of a mock hospital context study utilizing movement data.

The invention claimed is:

1. A method of total hygiene management comprising:
   determining, based on movement of a wearable computing device, at least one feature of movement that indicates a wearer of the wearable computing device is performing a cleaning action, thereby distinguishing movement of the wearable computing device during non-cleaning actions;
   determining, based on comparison of the feature of movement with reference to movement data associated with different types of cleaning actions, a specific type of cleaning action performed by the wearer of the wearable computing device;
   determining a quality of cleaning for the specific type of cleaning action performed by at least comparing movement data generated by the wearable device during the specific type of cleaning action with reference movement data associated with a threshold quality of cleaning for the specific type of cleaning action; and
   responsive to determining that the specific type of cleaning action performed by the wearer of the wearable computing device does not satisfy the threshold quality of cleaning, performing, by the wearable computing device, an operation.

2. The method of claim 1, wherein the specific type of cleaning action is selected from the group consisting of a floor surface cleaning action, an equipment cleaning action, and a hand hygiene cleaning action.

3. The method of claim 1, further comprising detecting, by the wearable computing device, movement associated with the wearable device during performance of a plurality of different types of cleaning actions.

4. The method of claim 3, wherein one of the plurality of different types of cleaning actions is a hand hygiene cleaning action and at least one other of the plurality of different types of cleaning actions is selected from the group consisting of a floor surface cleaning action, an equipment cleaning action, and combinations thereof.

5. The method of claim 4, wherein:
   the cleaning action is performed in a food preparation environment; and
   the at least one other of the plurality of different types of cleaning actions comprises an equipment cleaning action selected from the group consisting of a grill surface cleaning action, a fryer surface cleaning action, and combinations thereof.

6. The method of claim 4, wherein determining the quality of cleaning for the specific type of cleaning action performed comprises determining the quality of cleaning for each of the plurality of different types of cleaning actions performed.

7. The method of claim 4, further comprising:
   determining, based on the movement associated with the wearable computing device, a cleaning order in which the plurality of different types of cleaning actions were performed;
   comparing the cleaning order to a target order in which the plurality of different types of cleaning actions are expected to be performed; and
   responsive to determining that the plurality of different types of cleaning actions were not performed in the target order, at least one of:
      issuing, by the wearable computing device, a user alert; and
      storing cleaning order information associated with the plurality of different types of cleaning actions.

8. The method of claim 7, wherein the target order has the hand hygiene cleaning action following the other of the plurality of different types of cleaning actions.

9. The method of claim 1, further comprising, responsive to determining that the specific type of cleaning action performed by the wearer of the wearable computing device satisfies the threshold quality of cleaning, storing cleaning validation information associated with the specific type of cleaning action.

10. The method of claim 1, wherein determining, based on movement of the wearable computing device, at least one feature of movement that indicates the wearer of the wearable computing device is performing the cleaning action comprises:
    receiving movement data from at least a first sensor of the wearable computing device, first movement data corresponding to an acceleration of the wearable computing device and receiving, from at least a second sensor of the wearable computing device, second movement data corresponding to an angular velocity of the wearable computing device; and
    determining at least one signal feature of the movement data comprises determining at least one signal feature for the first movement data and at least one signal feature for the second movement data.

11. The method of claim 1, wherein the threshold quality of cleaning corresponds to at least one of a magnitude and a frequency of the at least one signal feature.

12. The method of claim 1, wherein the reference movement data associated with different types of cleaning actions and the reference movement data associated with the threshold quality of cleaning for the specific type of cleaning action are each generated from movement data obtained during one or more training episodes in which the wearer of the wearable computing device performs the specific type of cleaning action while wearing the wearable computing device or an equivalent thereof.

13. The method of claim 1, wherein performing the operation comprises issuing an alert via the wearable computing device indicating that the quality of cleaning is less than the threshold quality of cleaning, the alert being issued in substantially real-time with the specific type of cleaning action being performed.

14. The method of claim 1, wherein the wearable computing device is selected from the group consisting of a wristband device and an armband device.

15. The method of claim 1, wherein the wearable computing device is positionable in a pocket of an article of clothing worn by the individual performing cleaning.

16. The method of claim 1, wherein the wearable computing device comprises at least one of a graphical user interface and a haptic generator.

17. The method of claim 1, further comprising:
wirelessly transmitting movement data generated by the wearable computing device to one or more remote computing devices,
determining, at the one or more remote computing devices, at least one feature of movement that indicates the wearer of the wearable computing device is performing the cleaning action,
determining, at the one or more remote computing devices, the specific type of cleaning action performed by the wearer of the wearable computing device,
determining, at the one or more remote computing devices, the quality of cleaning for the specific type of cleaning action performed,
wireless transmitting from the one or more remote computing devices to the wearable computing device data indicating that the quality of cleaning for the specific type of cleaning action performed does not satisfy the threshold quality of cleaning, and
responsive to the wearable computing device receiving the data indicating that the quality of cleaning for the specific type of cleaning action performed does not satisfy the threshold quality of cleaning, performing, by the wearable computing device, the operation.

18. A wearable computing device comprising:
at least one sensor configured to detect movement associated with the wearable computing device;
at least one processor; and
a memory comprising instructions that, when executed, cause the at least one processor to:
receive, from the at least one sensor, movement data associated with the wearable computing device;
determine, based on the movement data, at least one feature of movement that indicates the individual wearing the wearable computing device is performing a cleaning action, thereby distinguishing movement of the wearable computing device during non-cleaning actions;
determine, based on comparison of the feature of movement with reference to movement data associated with different types of cleaning actions, a specific type of cleaning action performed by the wearer of the wearable computing device;
determine a quality of cleaning for the specific type of cleaning action performed by at least comparing the movement data generated during the specific type of cleaning action to reference movement data associated with a threshold quality of cleaning for the specific type of cleaning action,
responsive to determining that the specific type of cleaning action performed does not satisfy the threshold quality of cleaning, perform an operation.

19. The device of claim 18, wherein the instructions, when executed, cause the at least one processor to receive, from the at least one sensor, movement data while the individual wearing the wearable computing device performs a plurality of different types of cleaning actions.

20. The device of claim 19, wherein the instructions, when executed, cause the at least one processor to:
determine a hand hygiene cleaning action as one specific type of cleaning action performed by the wearer of the wearable computing device, and
determine at least one other specific type of cleaning action selected from the group consisting of a floor surface cleaning action, an equipment cleaning action, and combinations thereof.

21. The device of claim 19, wherein the instructions, when executed, cause the at least one processor to determine the quality of cleaning for the specific type of cleaning action performed by at least determining the quality of cleaning for each of the plurality of different types of cleaning actions performed.

22. The device of claim 19, wherein the instructions, when executed, cause the at least one processor to:
determine, based on the movement data, a cleaning order in which the plurality of different types of cleaning actions were performed;
compare the cleaning order to a target order in which the plurality of different types of cleaning actions are expected to be performed;
responsive to determining that the plurality of different types of cleaning actions were not performed in the target order, at least one of:
issue, by the wearable computing device, a user alert; and
store cleaning order information associated with the plurality of different types of cleaning actions in the memory.

23. The device of claim 18, wherein the instructions, when executed, cause the at least one processor to store cleaning validation information associated with the specific type of cleaning action.

24. The device of claim 18, wherein:
the at least one sensor comprises a first sensor configured to generate first movement data corresponding to an acceleration of the wearable computing device and a second sensor configured to generate second movement data corresponding to an angular velocity of the wearable computing device; and
the instructions, when executed, cause the at least one processor to determine the at least one signal feature for the movement data by at least determining a first signal feature for the first movement and a second signal feature for the second movement data.

25. The device of claim 18, wherein the threshold quality of cleaning for the target surface corresponds to at least one of a magnitude and a frequency of the at least one signal feature.

26. The device of claim 18, wherein the instructions, when executed, cause the at least one processor to perform the operation by at least issuing an alert via the wearable computing device indicating that the quality of cleaning is less than a threshold quality of cleaning, the alert being issued in substantially real-time with the individual performing the specific type of cleaning action being performed.

* * * * *